(12) United States Patent
Carls et al.

(10) Patent No.: US 8,252,031 B2
(45) Date of Patent: Aug. 28, 2012

(54) MOLDING DEVICE FOR AN EXPANDABLE INTERSPINOUS PROCESS IMPLANT

(75) Inventors: Thomas Carls, Memphis, TN (US); Kent M. Anderson, Memphis, TN (US); Eric C. Lange, Collierville, TN (US); Roy Lim, Memphis, TN (US); Hai H. Trieu, Cordova, TN (US); Aurelien Bruneau, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1631 days.

(21) Appl. No.: 11/414,445

(22) Filed: Apr. 28, 2006

(65) Prior Publication Data

US 2007/0270829 A1 Nov. 22, 2007

(51) Int. Cl.
*A61B 17/88* (2006.01)
*A61B 17/70* (2006.01)

(52) U.S. Cl. ........................................ 606/279; 606/249

(58) Field of Classification Search .................. 606/247, 606/248, 249; 623/17.11–17.16
See application file for complete search history.

(56) References Cited

U.S. PATENT DOCUMENTS

| | | |
|---|---|---|
| 1,870,942 A | 8/1932 | Beatty |
| 2,677,369 A | 5/1954 | Knowles |
| 3,108,595 A | 10/1963 | Overment |
| 3,397,699 A | 8/1968 | Kohl |
| 3,648,691 A | 3/1972 | Lumb et al. |
| 3,867,728 A | 2/1975 | Stubstad et al. |
| 4,003,376 A | 1/1977 | McKay et al. |
| 4,011,602 A | 3/1977 | Rybicki et al. |
| 4,078,559 A | 3/1978 | Nissinen |
| 4,257,409 A | 3/1981 | Bacal et al. |
| 4,327,736 A | 5/1982 | Inoue |
| 4,554,914 A | 11/1985 | Kapp et al. |
| 4,570,618 A | 2/1986 | Wu |
| 4,573,454 A | 3/1986 | Hoffman |
| 4,573,966 A | 3/1986 | Weikl et al. |
| 4,604,995 A | 8/1986 | Stephens et al. |
| 4,610,662 A | 9/1986 | Weikl et al. |
| 4,643,178 A | 2/1987 | Nastari et al. |
| 4,686,970 A | 8/1987 | Dove et al. |
| 4,721,103 A | 1/1988 | Freedland |
| 4,827,918 A | 5/1989 | Olerud |
| 4,932,975 A | 6/1990 | Main et al. |
| 4,936,848 A | 6/1990 | Bagby |
| 4,969,888 A | 11/1990 | Scholten et al. |
| 5,011,484 A | 4/1991 | Breard |
| 5,019,042 A | 5/1991 | Sahota |
| 5,047,055 A | 9/1991 | Bao et al. |

(Continued)

FOREIGN PATENT DOCUMENTS

DE 2821678 A1 11/1979

(Continued)

OTHER PUBLICATIONS

"Dispositivo Intervertebrale Ammortizzante DIAM," date unknown, p. 1.

(Continued)

*Primary Examiner* — Alvin Stewart
*Assistant Examiner* — David Comstock

(57) ABSTRACT

A molding device is disclosed and can include a first mold component and a second mold component substantially opposite the first mold component. The first mold component and the second mold component can fit around a superior spinous process and an inferior spinous process.

5 Claims, 34 Drawing Sheets

U.S. PATENT DOCUMENTS

| | | | |
|---|---|---|---|
| 5,092,866 | A | 3/1992 | Breard et al. |
| 5,112,306 | A | 5/1992 | Burton et al. |
| 5,171,280 | A | 12/1992 | Baumgartner |
| 5,201,734 | A | 4/1993 | Cozad et al. |
| 5,236,460 | A | 8/1993 | Barber |
| 5,242,444 | A | 9/1993 | MacMillan |
| 5,306,275 | A | 4/1994 | Bryan |
| 5,314,477 | A | 5/1994 | Marnay |
| 5,316,422 | A | 5/1994 | Coffman |
| 5,342,305 | A | 8/1994 | Shonk |
| 5,358,487 | A | 10/1994 | Miller |
| 5,360,430 | A | 11/1994 | Lin |
| 5,366,455 | A | 11/1994 | Dove |
| 5,415,661 | A | 5/1995 | Holmes |
| 5,437,672 | A | 8/1995 | Alleyne |
| 5,454,812 | A | 10/1995 | Lin |
| 5,460,610 | A | 10/1995 | Don Michael |
| 5,480,442 | A | 1/1996 | Bertagnoli |
| 5,496,318 | A * | 3/1996 | Howland et al. .............. 606/249 |
| 5,527,312 | A | 6/1996 | Ray |
| 5,549,679 | A | 8/1996 | Kuslich |
| 5,562,736 | A | 10/1996 | Ray et al. |
| 5,571,189 | A | 11/1996 | Kuslich |
| 5,609,634 | A | 3/1997 | Voydeville |
| 5,628,756 | A | 5/1997 | Barker, Jr. et al. |
| 5,645,597 | A | 7/1997 | Krapiva |
| 5,645,599 | A | 7/1997 | Samani |
| 5,665,122 | A | 9/1997 | Kambin |
| 5,674,295 | A | 10/1997 | Ray et al. |
| 5,676,702 | A | 10/1997 | Ratron |
| 5,690,649 | A | 11/1997 | Li |
| 5,702,452 | A | 12/1997 | Argenson et al. |
| 5,702,454 | A | 12/1997 | Baumgartner |
| 5,725,582 | A | 3/1998 | Bevan et al. |
| 5,746,762 | A | 5/1998 | Bass |
| 5,755,797 | A | 5/1998 | Baumgartner |
| 5,800,549 | A | 9/1998 | Bao et al. |
| 5,810,815 | A | 9/1998 | Morales |
| 5,836,948 | A | 11/1998 | Zucherman et al. |
| 5,860,977 | A | 1/1999 | Zucherman et al. |
| 5,964,730 | A | 10/1999 | Williams et al. |
| 5,976,186 | A | 11/1999 | Bao et al. |
| 6,019,792 | A | 2/2000 | Cauthen |
| 6,022,376 | A | 2/2000 | Assell et al. |
| 6,048,342 | A | 4/2000 | Zucherman et al. |
| 6,066,154 | A | 5/2000 | Reiley et al. |
| 6,068,630 | A | 5/2000 | Zucherman et al. |
| 6,074,390 | A | 6/2000 | Zucherman et al. |
| 6,102,922 | A | 8/2000 | Jakobsson et al. |
| 6,132,464 | A | 10/2000 | Martin |
| 6,179,874 | B1 | 1/2001 | Cauthen |
| 6,214,037 | B1 | 4/2001 | Mitchell et al. |
| 6,238,397 | B1 | 5/2001 | Zucherman et al. |
| 6,245,107 | B1 | 6/2001 | Ferree |
| 6,277,120 | B1 | 8/2001 | Lawson |
| 6,293,949 | B1 | 9/2001 | Justis et al. |
| 6,299,613 | B1 | 10/2001 | Ogilvie et al. |
| 6,332,894 | B1 | 12/2001 | Stalcup et al. |
| 6,336,930 | B1 | 1/2002 | Stalcup et al. |
| 6,352,537 | B1 | 3/2002 | Strnad |
| 6,364,883 | B1 | 4/2002 | Santilli |
| 6,395,034 | B1 | 5/2002 | Suddaby |
| 6,402,750 | B1 | 6/2002 | Atkinson et al. |
| 6,402,785 | B1 | 6/2002 | Zdeblick et al. |
| 6,419,703 | B1 | 7/2002 | Fallin et al. |
| 6,419,704 | B1 | 7/2002 | Ferree |
| 6,425,923 | B1 | 7/2002 | Stalcup et al. |
| 6,432,130 | B1 | 8/2002 | Hanson |
| 6,440,168 | B1 | 8/2002 | Cauthen |
| 6,440,169 | B1 | 8/2002 | Elberg et al. |
| 6,447,514 | B1 | 9/2002 | Stalcup et al. |
| 6,451,019 | B1 | 9/2002 | Zucherman et al. |
| 6,500,178 | B2 | 12/2002 | Zucherman et al. |
| 6,514,256 | B2 | 2/2003 | Zucherman et al. |
| 6,558,390 | B2 | 5/2003 | Cragg |
| 6,582,433 | B2 | 6/2003 | Yun |
| 6,610,069 | B2 | 8/2003 | Euteneuer et al. |
| 6,626,944 | B1 | 9/2003 | Taylor |
| 6,645,207 | B2 | 11/2003 | Dixon et al. |
| 6,645,248 | B2 | 11/2003 | Casutt |
| 6,669,729 | B2 | 12/2003 | Chin |
| 6,695,842 | B2 | 2/2004 | Zucherman et al. |
| 6,699,246 | B2 | 3/2004 | Zucherman et al. |
| 6,709,435 | B2 | 3/2004 | Lin |
| 6,723,126 | B1 | 4/2004 | Berry |
| 6,733,533 | B1 | 5/2004 | Lozier |
| 6,733,534 | B2 * | 5/2004 | Sherman ................... 623/17.16 |
| 6,761,720 | B1 | 7/2004 | Senegas |
| 6,805,697 | B1 | 10/2004 | Helm et al. |
| 6,835,205 | B2 | 12/2004 | Atkinson et al. |
| 6,852,128 | B2 | 2/2005 | Lange |
| 6,863,688 | B2 | 3/2005 | Ralph et al. |
| 6,899,713 | B2 | 5/2005 | Shaolian et al. |
| 6,902,580 | B2 | 6/2005 | Fallin et al. |
| 6,946,000 | B2 | 9/2005 | Senegas et al. |
| 6,958,077 | B2 | 10/2005 | Suddaby |
| 6,969,404 | B2 | 11/2005 | Ferree |
| 6,969,405 | B2 | 11/2005 | Suddaby |
| 6,972,036 | B2 | 12/2005 | Boehm, Jr. et al. |
| 7,041,136 | B2 | 5/2006 | Goble et al. |
| 7,048,736 | B2 | 5/2006 | Robinson et al. |
| 7,081,120 | B2 | 7/2006 | Li et al. |
| 7,087,083 | B2 | 8/2006 | Pasquet et al. |
| 7,097,654 | B1 | 8/2006 | Freedland |
| 7,101,375 | B2 | 9/2006 | Zucherman et al. |
| 7,105,024 | B2 | 9/2006 | Richelsoph |
| 7,163,558 | B2 | 1/2007 | Senegas et al. |
| 7,201,751 | B2 | 4/2007 | Zucherman et al. |
| 7,238,204 | B2 | 7/2007 | Le Couedic et al. |
| 7,306,628 | B2 | 12/2007 | Zucherman et al. |
| 7,335,203 | B2 | 2/2008 | Winslow et al. |
| 7,377,942 | B2 | 5/2008 | Berry |
| 7,442,208 | B2 | 10/2008 | Mathieu et al. |
| 7,442,210 | B2 | 10/2008 | Segal et al. |
| 7,445,637 | B2 | 11/2008 | Taylor |
| 7,582,106 | B2 | 9/2009 | Teitelbaum et al. |
| 7,604,652 | B2 | 10/2009 | Arnin et al. |
| 7,658,752 | B2 | 2/2010 | Labrom et al. |
| 7,666,205 | B2 | 2/2010 | Weikel et al. |
| 7,749,252 | B2 | 7/2010 | Zucherman et al. |
| 7,771,456 | B2 | 8/2010 | Hartmann et al. |
| 7,824,431 | B2 | 11/2010 | McCormack |
| 7,862,615 | B2 | 1/2011 | Carli et al. |
| 7,901,430 | B2 | 3/2011 | Matsuura et al. |
| 7,942,847 | B2 | 5/2011 | Stupecky et al. |
| 2001/0016743 | A1 | 8/2001 | Zucherman et al. |
| 2002/0029039 | A1 | 3/2002 | Zucherman et al. |
| 2002/0082600 | A1 | 6/2002 | Shaolian et al. |
| 2002/0133155 | A1 | 9/2002 | Ferree |
| 2002/0143331 | A1 | 10/2002 | Zucherman et al. |
| 2002/0177866 | A1 | 11/2002 | Weikel et al. |
| 2003/0040746 | A1 | 2/2003 | Mitchell et al. |
| 2003/0045940 | A1 | 3/2003 | Eberlein et al. |
| 2003/0065330 | A1 | 4/2003 | Zucherman et al. |
| 2003/0139814 | A1 | 7/2003 | Bryan |
| 2003/0153915 | A1 | 8/2003 | Nekozuka et al. |
| 2003/0220649 | A1 | 11/2003 | Bao et al. |
| 2004/0055607 | A1 | 3/2004 | Boehm, Jr. et al. |
| 2004/0064094 | A1 | 4/2004 | Freyman |
| 2004/0083002 | A1 | 4/2004 | Belef et al. |
| 2004/0097931 | A1 | 5/2004 | Mitchell |
| 2004/0106995 | A1 | 6/2004 | Le Couedic et al. |
| 2004/0117017 | A1 | 6/2004 | Pasquet et al. |
| 2004/0133280 | A1 | 7/2004 | Trieu |
| 2004/0186475 | A1 | 9/2004 | Falahee |
| 2004/0186576 | A1 | 9/2004 | Biscup et al. |
| 2004/0199255 | A1 | 10/2004 | Mathieu et al. |
| 2004/0215342 | A1 | 10/2004 | Suddaby |
| 2004/0225360 | A1 | 11/2004 | Malone |
| 2004/0230305 | A1 | 11/2004 | Gorensek et al. |
| 2004/0260239 | A1 | 12/2004 | Kusleika |
| 2005/0010293 | A1 | 1/2005 | Zucherman et al. |
| 2005/0015140 | A1 | 1/2005 | deBeer |
| 2005/0033431 | A1 | 2/2005 | Gordon et al. |
| 2005/0033432 | A1 | 2/2005 | Gordon et al. |
| 2005/0033434 | A1 | 2/2005 | Berry |
| 2005/0033437 | A1 | 2/2005 | Bao et al. |

| | | |
|---|---|---|
| 2005/0033439 A1 | 2/2005 | Gordon et al. |
| 2005/0038432 A1 | 2/2005 | Shaolian et al. |
| 2005/0049708 A1 | 3/2005 | Atkinson et al. |
| 2005/0056292 A1 | 3/2005 | Cooper |
| 2005/0101955 A1 | 5/2005 | Zucherman et al. |
| 2005/0143738 A1 | 6/2005 | Zucherman et al. |
| 2005/0165398 A1 | 7/2005 | Reiley |
| 2005/0197702 A1 | 9/2005 | Coppes et al. |
| 2005/0203512 A1 | 9/2005 | Hawkins et al. |
| 2005/0203624 A1 | 9/2005 | Serhan et al. |
| 2005/0203626 A1 | 9/2005 | Sears et al. |
| 2005/0209696 A1 | 9/2005 | Lin et al. |
| 2005/0216017 A1 | 9/2005 | Fielding et al. |
| 2005/0228391 A1 | 10/2005 | Levy et al. |
| 2005/0240267 A1 | 10/2005 | Randall et al. |
| 2005/0261768 A1 | 11/2005 | Trieu |
| 2005/0267579 A1 | 12/2005 | Reiley et al. |
| 2005/0267580 A1 | 12/2005 | Suddaby |
| 2005/0273110 A1 | 12/2005 | Boehm, Jr. et al. |
| 2005/0288672 A1 | 12/2005 | Ferree |
| 2006/0004367 A1 | 1/2006 | Alamin et al. |
| 2006/0004447 A1 | 1/2006 | Mastrorio et al. |
| 2006/0015181 A1 | 1/2006 | Elberg |
| 2006/0015183 A1 | 1/2006 | Gilbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0106381 A1 | 5/2006 | Ferree et al. |
| 2006/0106397 A1 | 5/2006 | Lins |
| 2006/0111728 A1 | 5/2006 | Abdou |
| 2006/0122620 A1 | 6/2006 | Kim |
| 2006/0129239 A1 | 6/2006 | Kwak |
| 2006/0136060 A1* | 6/2006 | Taylor ........................ 623/17.13 |
| 2006/0149136 A1 | 7/2006 | Seto et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235532 A1 | 10/2006 | Meunier et al. |
| 2006/0241613 A1 | 10/2006 | Bruneau et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0043362 A1 | 2/2007 | Malandain et al. |
| 2007/0043363 A1 | 2/2007 | Malandain et al. |
| 2007/0088436 A1 | 4/2007 | Parsons et al. |
| 2007/0100340 A1 | 5/2007 | Lange et al. |
| 2007/0112330 A1 | 5/2007 | Palasis |
| 2007/0123861 A1 | 5/2007 | Dewey et al. |
| 2007/0162000 A1 | 7/2007 | Perkins |
| 2007/0162136 A1 | 7/2007 | O'Neil et al. |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0198091 A1 | 8/2007 | Boyer et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276496 A1 | 11/2007 | Lange et al. |
| 2007/0276497 A1 | 11/2007 | Anderson |
| 2008/0021460 A1 | 1/2008 | Bruneau et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0195152 A1 | 8/2008 | Altarac et al. |
| 2008/0208341 A1 | 8/2008 | McCormack et al. |
| 2008/0215094 A1 | 9/2008 | Taylor |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0105773 A1 | 4/2009 | Lange et al. |
| 2009/0240283 A1 | 9/2009 | Carls et al. |
| 2009/0326538 A1 | 12/2009 | Sennett et al. |
| 2010/0121379 A1 | 5/2010 | Edmond |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |
| 2010/0318190 A1 | 12/2010 | Collins et al. |

FOREIGN PATENT DOCUMENTS

| | | |
|---|---|---|
| DE | 101 49 385 A1 | 4/2003 |
| EP | 0418387 A1 | 3/1991 |
| EP | 0322334 B1 | 2/1992 |
| EP | 0 661 957 B1 | 9/1998 |
| EP | 1138268 A1 | 10/2001 |
| EP | 1330987 A1 | 7/2003 |
| EP | 1854433 A1 | 11/2007 |
| EP | 1905392 A1 | 4/2008 |
| FR | 2623085 A1 | 5/1989 |
| FR | 2625097 A1 | 6/1989 |
| FR | 2681525 A | 3/1993 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A | 1/1996 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2775183 A1 | 8/1999 |
| FR | 2799640 A | 4/2001 |
| FR | 2799948 A1 | 4/2001 |
| FR | 2816197 A1 | 5/2002 |
| FR | 2851154 A | 8/2004 |
| JP | 02-224660 | 9/1990 |
| JP | 09-075381 | 3/1997 |
| JP | 2003-079649 | 3/2003 |

| | | |
|---|---|---|
| SU | 988281 | 1/1983 |
| SU | 1484348 A1 | 6/1989 |
| WO | WO 91/13598 | 9/1991 |
| WO | WO 94/26192 | 11/1994 |
| WO | WO 94/26195 | 11/1994 |
| WO | WO 98/20939 | 5/1998 |
| WO | WO 98/34568 | 8/1998 |
| WO | WO 99/59669 | 11/1999 |
| WO | WO 00/45752 | 8/2000 |
| WO | WO 01/15638 A1 | 3/2001 |
| WO | WO 02/09625 A1 | 2/2002 |
| WO | WO 03/007829 | 1/2003 |
| WO | WO 2004/028401 A2 | 4/2004 |
| WO | WO 2004/047691 A1 | 6/2004 |
| WO | 2004/084768 A | 10/2004 |
| WO | WO 2004/084743 A1 | 10/2004 |
| WO | WO 2004/084768 A2 | 10/2004 |
| WO | 2005/002474 A | 1/2005 |
| WO | WO 2005/002474 A1 | 1/2005 |
| WO | 2005/009300 A | 2/2005 |
| WO | WO 2005/009300 A1 | 2/2005 |
| WO | WO 2005/016194 A2 | 2/2005 |
| WO | WO 2005/044118 A1 | 5/2005 |
| WO | WO 2005/097004 A2 | 10/2005 |
| WO | WO 2005/110258 A1 | 11/2005 |
| WO | WO 2005/115261 A1 | 12/2005 |
| WO | WO 2006/009855 A2 | 1/2006 |
| WO | 2006/025815 A | 3/2006 |
| WO | 2006/044786 A | 4/2006 |
| WO | WO 2006/064356 A1 | 6/2006 |
| WO | 2006/089085 A | 8/2006 |
| WO | WO 2007/034516 A1 | 3/2007 |
| WO | 2007/075788 A | 7/2007 |

OTHER PUBLICATIONS

"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," Spine, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Duff, "Methyl Methacrylate in Spinal Stabilization," Techniques in Spinal Fusion and Stabilization, Hitchon et al., eds., 1995, pp. 147-151, Ch. 14, Thieme, New York.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.
Fassio, "Mise au Point Sur la Ligamentoplastie Inter-Epineuse Lombaire Dans les Instabilites," Maîtrise Orthopédique, Jul. 1993, pp. 18, No. 25.
Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.
Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.
Hambly et al., "Tension Band Wiring-Bone Grafting for Spondylolysis and Spondylolisthesis," SPINE, 1989, pp. 455-460, vol. 14, No. 4.
Kiwerski, "Rehabilitation of Patients with Thoracic Spine Injury Treated by Spring Alloplasty," Int. J. Rehab. Research, 1983, pp. 469-474, vol. 6, No. 4.
Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.
Mah et al., "Threaded K-Wire Spinous Process Fixation of the Axis for Modified Gallie Fusion in Children and Adolescents," J. Pediatric Othopaedics, 1989, pp. 675-679, vol. 9.
Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.
McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.
Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.
Müller, "Restauration Dynamique de la Stabilité Rachidienne," Tiré de la Sulzer Technical Review, Jan. 1999, Sulzer Management Ltd, Winterthur, Switzerland.
Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.
Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90° Congresso, Jun. 21-23, 2001, Paestum.
Petrini et al., "Stabilizzazione Elastica," Patologia Degenerativa del Rachide Lombare, Oct. 5-6, 2001, Rimini.
Porter, "Spinal Stenosis and Neurogenic Claudication," SPINE, Sep. 1, 1996, pp. 2046-2052, vol. 21, No. 17.
Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.
Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.
Richards et al., "The Treatment Mechanism of an Interspinous Process Implant for Lumbar Neurogenic Intermittent Claudication," SPINE, 2005, pp. 744-749, vol. 30, No. 7.
Scarfò, "Instability/Stenosis: Holistic Approach for Less Invasive Surgery," date unknown, University of Siena, Siena, Italy.
Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.
Schlegel et al., "The Role of Distraction in Improving the Space Available in the Lumbar Stenotic Canal and Foramen," SPINE, 1994, pp. 2041-2047, vol. 19, No. 18.
Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.
Senegas et al., "Stabilisation Lombaire Souple," Instabilité Vertébrales Lombaires, Gastambide, ed., 1995, pp. 122-132, Expansion Scientifique Française, Paris, France.
Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "DIAM—Modified CAD Geometry and Meshing," date unknown.

Taylor et al., "Analyse d'une expérience clinique d'un implant postérieur amortissant," Rachis Revue de Pathologie Vertébrale, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

U.S. Appl. No. 11/442,621, filed May 26, 2006, Allard et al.

U.S. Appl. No. 11/481,079, filed Jul. 5, 2006, Anderson et al.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine After Dynamic Stabilization," J. Spinal Disord. Tech., 2006, vol. 00, No. 00, pp. 1-7.

Buric et al., "DIAM device for Low Back Pain in Degenerative Disc Disease 24 Months Follow-up," Acta Neurochirurgica Supplementum, 2011, vol. 108, pp. 177-182.

Kramer et al., "Intervetertebral Disk Diseases: Causes, Diagnosis, Treatment and Prophylaxis," pp. 244-249, Medical, 1990.

Phillips et al., "Biomechanics of Posterior Dynamic Stabilizing Device (DIAM) After Facetectomy and Discectomy," The Spine Journal, 2006, vol. 6, pp. 714-722.

Taylor et al., "Device for Intervertebral Assisted Motion: Technique and Initial Results," Neurosurg. Focus, Jan. 2007, vol. 22, pp. 1-6.

Wilke et al., "Biomechanical Effect of Different Lumbar Interspinous Implants on Flexibility and Intradiscal Pressure," Eur. Spine J., vol. 17, published online Jun. 27, 2008, pp. 1049-1056.

Zdeblick et al., "Two-Point Fixation of the Lumbar Spine Differential Stability in Rotation," SPINE, 1991, pp. S298-S301, vol. 16, No. 6, Supplement.

Zhao et al., ""Efficacy of the Dynamic Interspirous Assisted Motion System in Clinical Treatment of Degenerative Lumbar Disease,""Chin. Med. J., 2010, 123(21), pp. 2974-2977.

\* cited by examiner

US 8,252,031 B2

MOLDING DEVICE FOR AN EXPANDABLE INTERSPINOUS PROCESS IMPLANT

FIELD OF THE DISCLOSURE

The present disclosure relates generally to orthopedics and orthopedic surgery. More specifically, the present disclosure relates to devices used to support adjacent spinous processes.

BACKGROUND

In human anatomy, the spine is a generally flexible column that can take tensile and compressive loads. The spine also allows bending motion and provides a place of attachment for keels, muscles and ligaments. Generally, the spine is divided into three sections: the cervical spine, the thoracic spine and the lumbar spine. The sections of the spine are made up of individual bones called vertebrae. Also, the vertebrae are separated by intervertebral discs, which are situated between adjacent vertebrae.

The intervertebral discs function as shock absorbers and as joints. Further, the intervertebral discs can absorb the compressive and tensile loads to which the spinal column may be subjected. At the same time, the intervertebral discs can allow adjacent vertebral bodies to move relative to each other a limited amount, particularly during bending, or flexure, of the spine. Thus, the intervertebral discs are under constant muscular and/or gravitational pressure and generally, the intervertebral discs are the first parts of the lumbar spine to show signs of deterioration.

Facet joint degeneration is also common because the facet joints are in almost constant motion with the spine. In fact, facet joint degeneration and disc degeneration frequently occur together. Generally, although one may be the primary problem while the other is a secondary problem resulting from the altered mechanics of the spine, by the time surgical options are considered, both facet joint degeneration and disc degeneration typically have occurred. For example, the altered mechanics of the facet joints and/or intervertebral disc may cause spinal stenosis, degenerative spondylolisthesis, and degenerative scoliosis.

DETAILED DESCRIPTION OF THE DRAWINGS

A molding device is disclosed and can include a first mold component and a second mold component substantially opposite the first mold component. The first mold component and the second mold component can fit around a superior spinous process and an inferior spinous process.

In still another embodiment, a molding device is disclosed and can include a first mold component and a second mold component substantially opposite the first mold component. The first mold component and the second mold component can be rotated between an open position and a closed position.

Further, the molding device can be placed around an unmolded implant, a superior spinous process, and an inferior spinous process.

In another embodiment, a kit for field use is disclosed and can include a molding device that can be placed around a superior spinous process and an inferior spinous process. Also, the kit can include an expandable interspinous process implant that can be placed between the superior spinous process and the inferior spinous process within the molding device.

In yet another embodiment, a kit for field use is disclosed and can include an unmolded interspinous process implant that can be placed between a superior spinous process and an inferior spinous process. Additionally, the kit can include a molding device that can be placed around the unmolded interspinous process implant.

In another embodiment, a molding device is disclosed and can include a first arm and a first mold can be component attached to the first arm. Further, the molding device can include a second arm substantially opposite the first arm and a second mold component can be attached to the second arm. The first mold component and the second mold component can fit around a superior spinous process and an inferior spinous process.

In yet another embodiment, a molding device is disclosed and can include a first arm and a first mold component can be attached to the first arm. The molding device can also include a second arm substantially opposite the first arm and a second mold component can be attached to the second arm. Moreover, the molding device can be rotated between an open position and a closed position. In the closed position, the molding device can be placed around an implant, a superior spinous process, and an inferior spinous process.

In still another embodiment, a method of treating a spine is disclosed and can include installing an expandable interspinous process implant between a superior spinous process and an inferior spinous process and installing a molding device around the expandable interspinous process. Further, the method can include expanding the expandable interspinous process implant to distract the superior spinous process and the inferior spinous process.

Description of Relevant Anatomy

Figure 1:
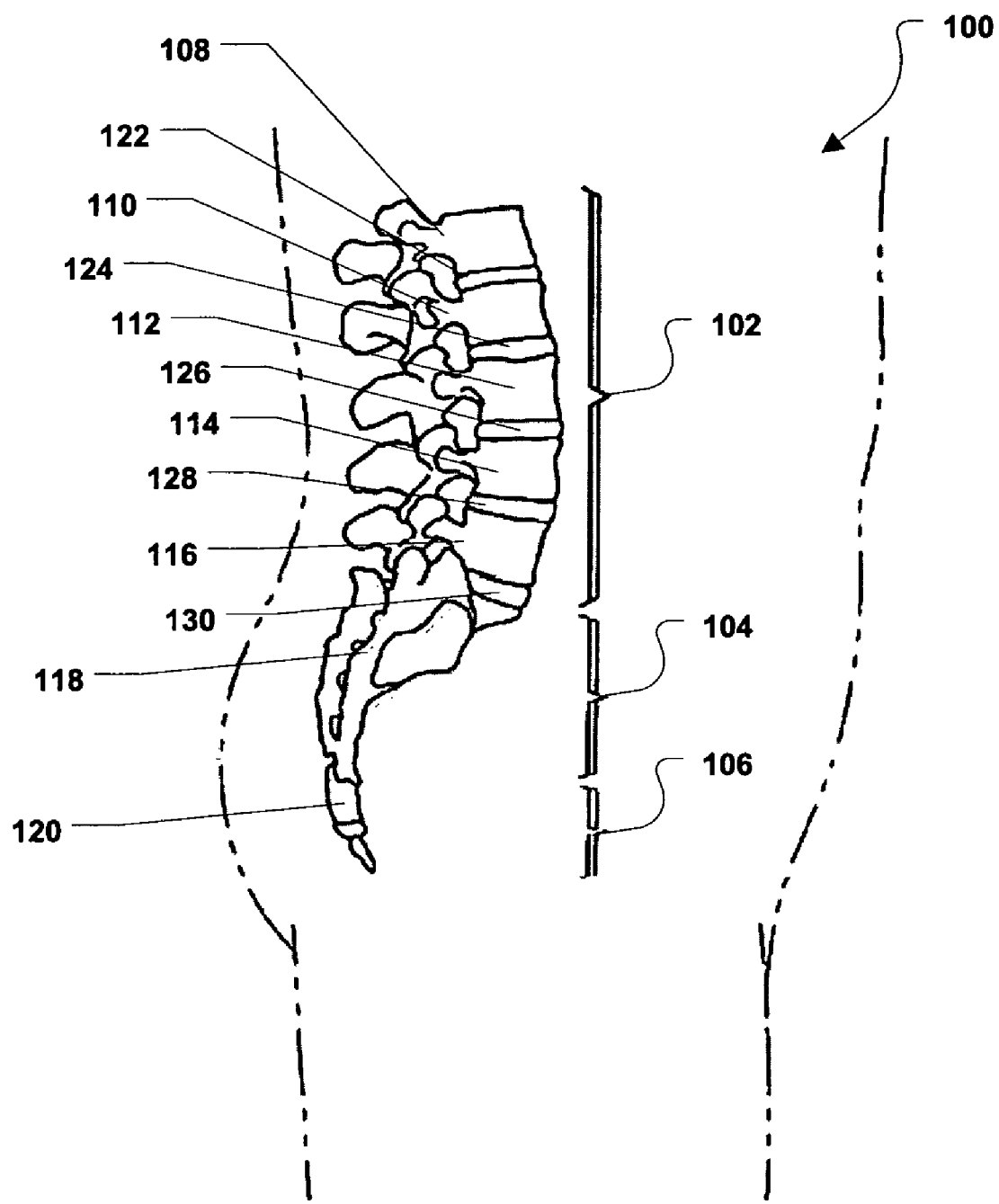
FIG. 1 is a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. As is known in the art, the vertebral column 100 also includes a cervical region and a thoracic region. For clarity and ease of discussion, the cervical region and the thoracic region are not illustrated.

As shown in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, damaged, or otherwise in need of repair, augmentation or treatment, that intervertebral lumbar disc 122, 124, 126, 128, 130 can be treated in accordance with one or more of the embodiments described herein.

Figure 2:
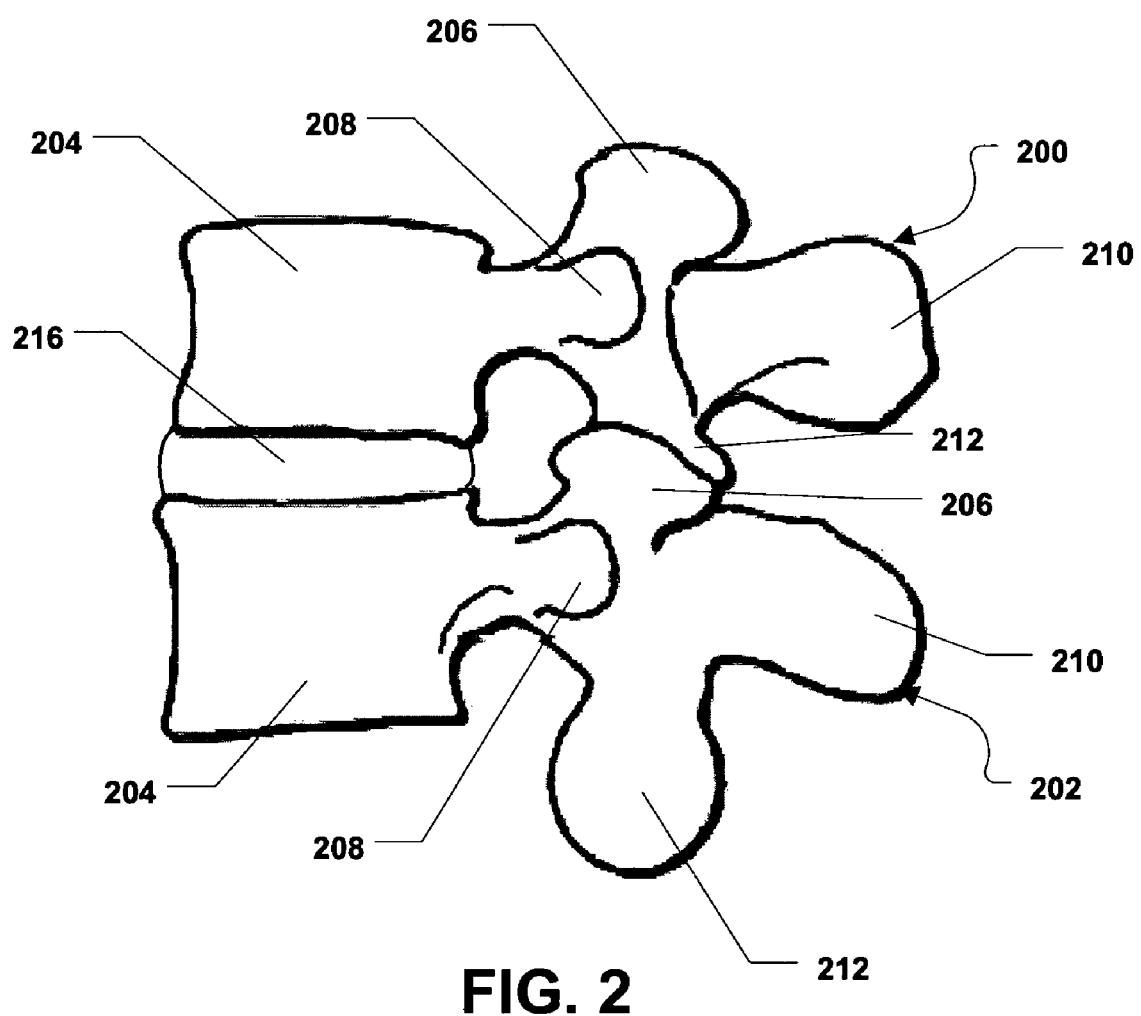
FIG. 2 is a lateral view of a pair of adjacent vertebrae.

FIG. 2 depicts a detailed lateral view of two adjacent vertebrae, e.g., two of the lumbar vertebra 108, 110, 112, 114, 116 shown in FIG. 1. FIG. 2 illustrates a superior vertebra 200 and an inferior vertebra 202. As shown, each vertebra 200, 202 includes a vertebral body 204, a superior articular process 206, a transverse process 208, a spinous process 210 and an inferior articular process 212. FIG. 2 further depicts an intervertebral disc 216 between the superior vertebra 200 and the inferior vertebra 202. As described in greater detail below, a collagen material according to one or more of the embodiments described herein can be injected within the intervertebral disc 216 to treat a degenerative or otherwise deleterious condition.

Figure 3:
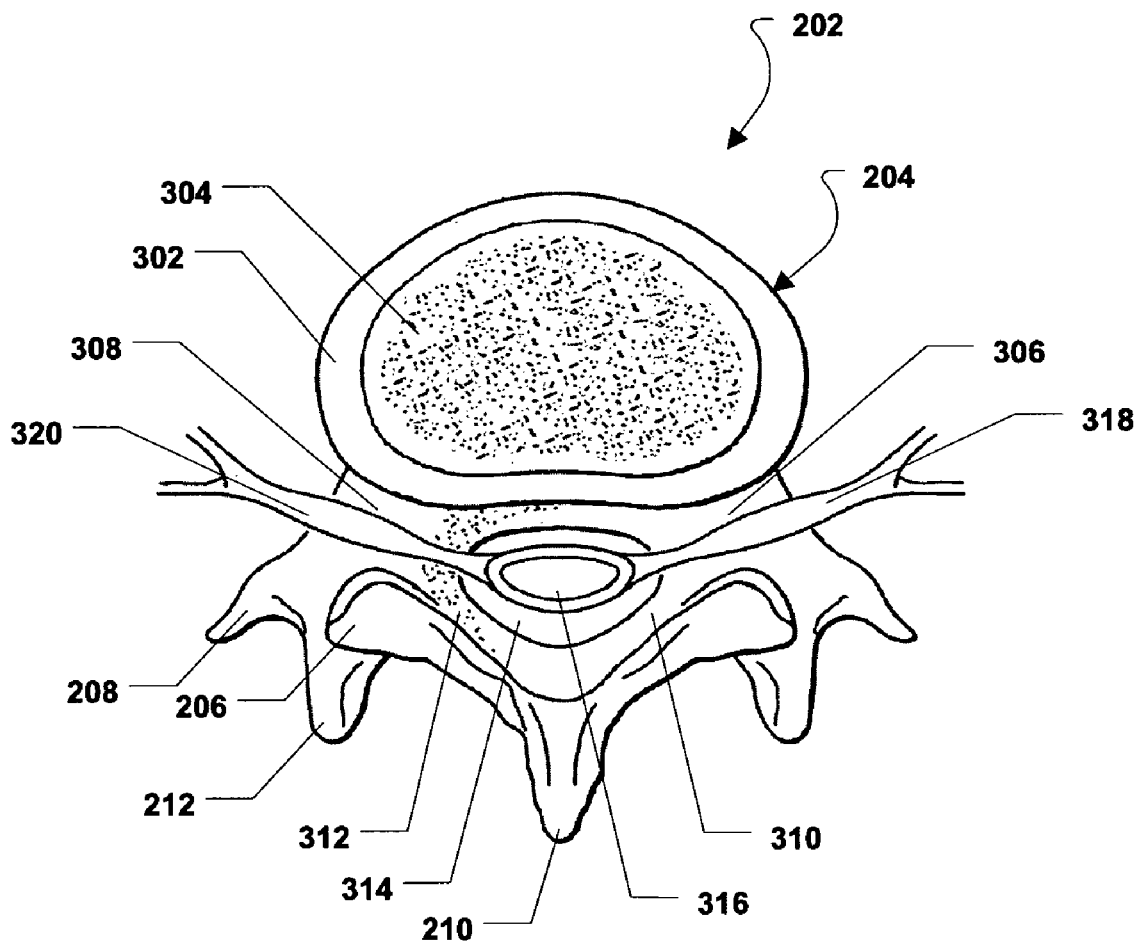
FIG. 3 is a top plan view of a vertebra.

Referring to FIG. 3, a vertebra, e.g., the inferior vertebra 202 (FIG. 2), is illustrated. As shown, the vertebral body 204 of the inferior vertebra 202 includes a cortical rim 302 composed of cortical bone. Also, the vertebral body 204 includes cancellous bone 304 within the cortical rim 302. The cortical rim 302 is often referred to as the apophyseal rim or apophyseal ring. Further, the cancellous bone 304 is softer than the cortical bone of the cortical rim 302.

As illustrated in FIG. 3, the inferior vertebra 202 further includes a first pedicle 306, a second pedicle 308, a first lamina 310, and a second lamina 312. Further, a vertebral foramen 314 is established within the inferior vertebra 202. A spinal cord 316 passes through the vertebral foramen 314. Moreover, a first nerve root 318 and a second nerve root 320 extend from the spinal cord 316.

It is well known in the art that the vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2 and FIG. 3. The first and second cervical vertebrae are structurally different than the rest of the vertebrae in order to support a skull.

Description of a First Embodiment of an Expandable Interspinous Process Implant

Figure 4:
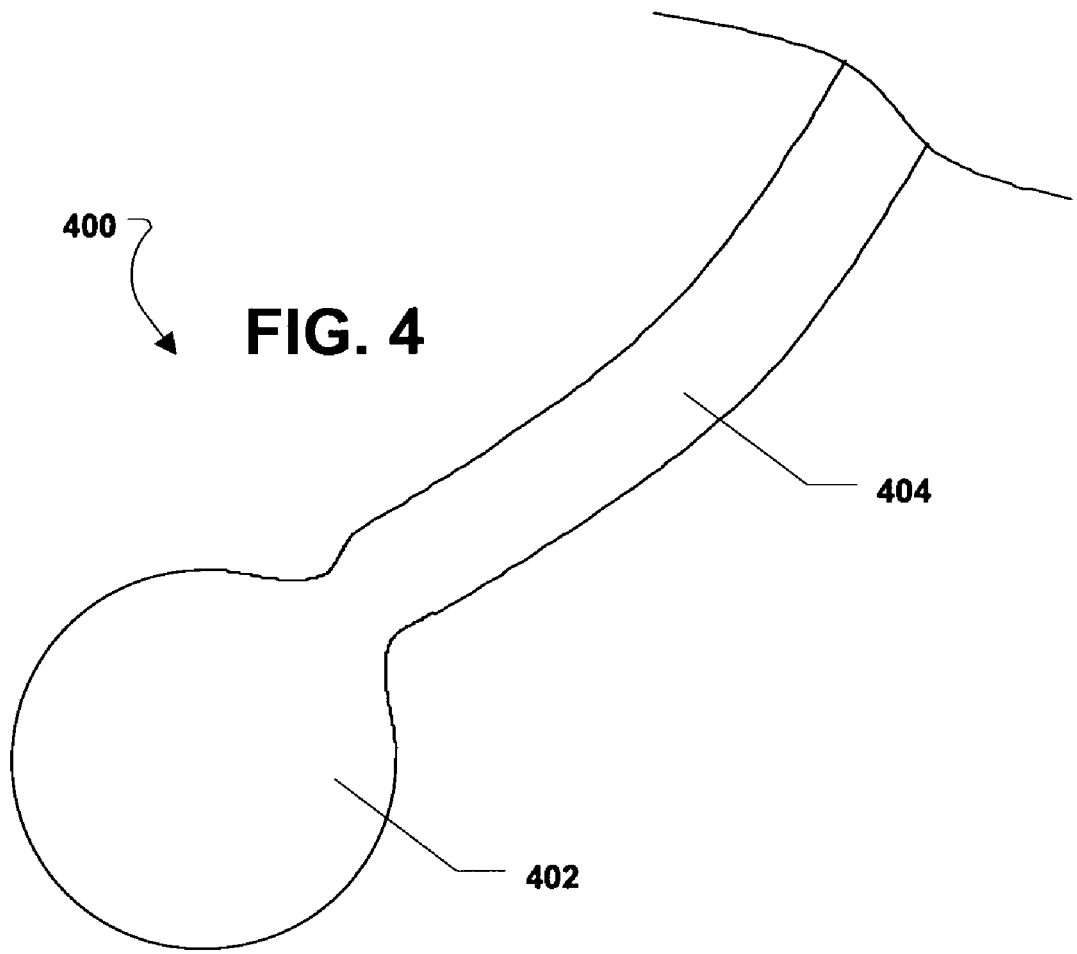
FIG. 4 is a view of a first expandable interspinous process implant in a relaxed configuration.
Figure 5:
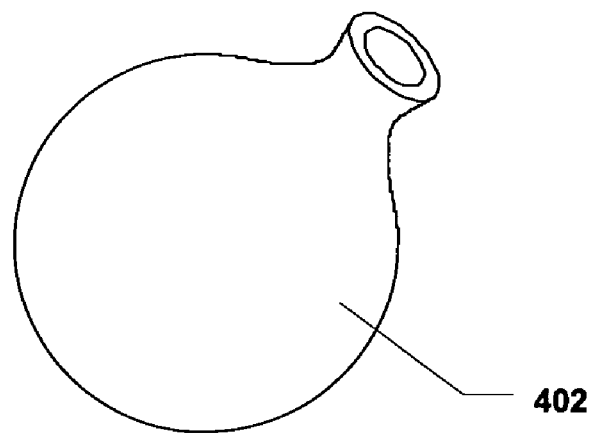
FIG. 5 is a view of the first expandable interspinous process implant with an injection tube removed.

Referring to FIG. 4 and FIG. 5, a first expandable interspinous process implant is shown and is generally designated 400. As shown, the expandable interspinous process implant can include a hollow, expandable body 402. In a particular embodiment, the expandable body 402 can be made from one or more elastic biocompatible materials. For example, the materials can be silicone, polyurethane, polycarbonate urethane, polyethylene terephthalate, silicone copolymers, polyolefin, or any combination thereof.

As illustrated in FIG. 4, the expandable interspinous process implant 400 can further include an injection tube 404. FIG. 5 indicates that the injection tube 404 can be removed, e.g., after the expandable interspinous process implant 400 is inflated.

In a particular embodiment, the expandable interspinous process implant 400 can be injected with one or more injectable biocompatible materials that become substantially rigid after curing. Further, the injectable biocompatible materials can include polymer materials that become substantially rigid yet remain elastic after curing. Also, the injectable biocompatible materials can include ceramics.

For example, the polymer materials can include polyurethane, polyolefin, silicone, silicone polyurethane copolymers, polymethylmethacrylate, epoxy, cyanoacrylate, hydrogels, resorbable polymers, or a combination thereof. Further, the polyolefin materials can include polypropylene, polyethylene, halogenated polyolefin, and flouropolyolefin.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl)oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof. The resorbable polymers can include polylactide (PLA), polyglycolide (PGA), polylactide-co-glycolide (PLG), Poly-e-caprolactone, polydiaoxanone, polyanhydride, trimethylene carbonate, poly-β-hydroxybutyrate (PHB), poly-g-ethyl glutamate, poly-DTH-iminocarbonate, poly-bisphenol-A-iminocarbonate), polyorthoester (POE), polyglycolic lactic acid (PGLA), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air. In certain embodiments, the body can be provided with a seal (not shown) or one way valve (not shown) to maintain the injectable biocompatible material within the body.

Figure 6:
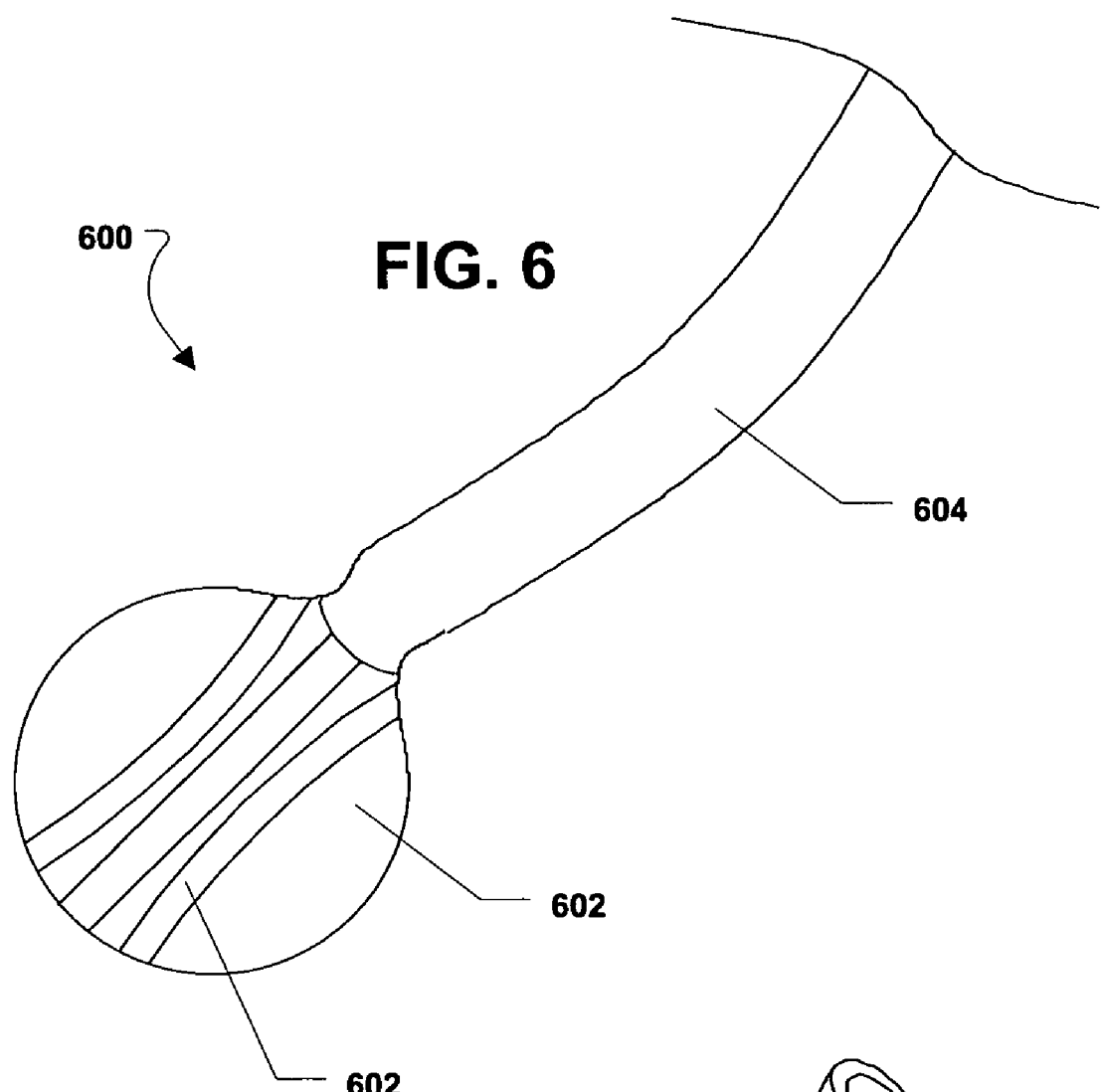
FIG. 6 is a view of a second expandable interspinous process implant in a relaxed configuration.
Figure 7:
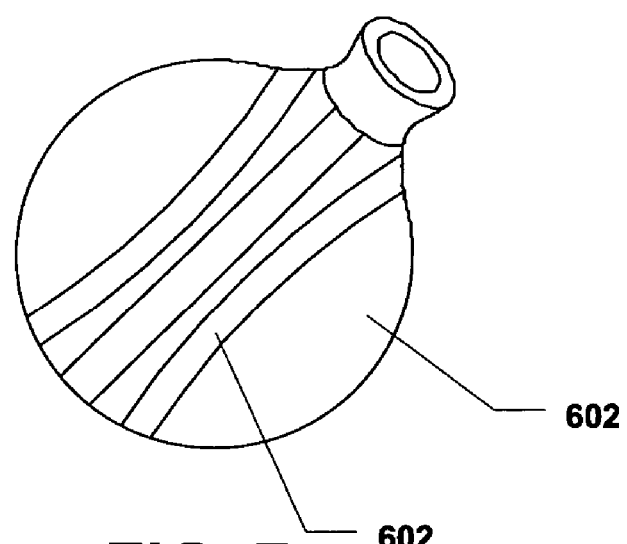
FIG. 7 is a view of the second expandable interspinous process implant with an injection tube removed.

Description of a Second Embodiment of an Expandable Interspinous Process Implant Referring to FIG. 6 and FIG. 7, a second expandable interspinous process implant is shown and is generally designated 600. As shown, the expandable interspinous process implant can include a hollow, expandable body 602. In a particular embodiment, the expandable body 602 can be made from one or more elastic biocompatible materials. For example, the materials can be silicone, polyurethane, polycarbonate urethane, polyethylene terephthalate, silicone copolymers, polyolefin, or any combination thereof.

As illustrated in FIG. 6, the expandable interspinous process implant 600 can further include an injection tube 604. FIG. 7 indicates that the injection tube 604 can be removed, e.g., after the expandable interspinous process implant 600 is inflated.

In a particular embodiment, the expandable interspinous process implant 600 can be injected with one or more injectable biocompatible materials that become substantially rigid after curing. Further, the injectable biocompatible materials can include polymer materials that become substantially rigid yet remain elastic after curing. Also, the injectable biocompatible materials can include ceramics.

For example, the polymer materials can include polyurethane, polyolefin, silicone, silicone polyurethane copolymers, polymethylmethacrylate, epoxy, cyanoacrylate, hydrogels, resorbable polymers, or a combination thereof. Further, the polyolefin materials can include polypropylene, polyethylene, halogenated polyolefin, and flouropolyolefin.

The hydrogels can include polyacrylamide (PAAM), poly-N-isopropylacrylamine (PNIPAM), polyvinyl methylether (PVM), polyvinyl alcohol (PVA), polyethyl hydroxyethyl cellulose, poly(2-ethyl)oxazoline, polyethyleneoxide (PEO), polyethylglycol (PEG), polyacrylacid (PAA), polyacrylonitrile (PAN), polyvinylacrylate (PVA), polyvinylpyrrolidone (PVP), or a combination thereof. The resorbable polymers can include polylactide (PLA), polyglycolide (PGA), polylactide-co-glycolide (PLG), Poly-e-caprolactone, polydiaoxanone, polyanhydride, trimethylene carbonate, poly-β-hydroxybutyrate (PHB), poly-g-ethyl glutamate, poly-DTH-iminocarbonate, poly-bisphenol-A-iminocarbonate), polyorthoester (POE), polyglycolic lactic acid (PGLA), or a combination thereof.

In a particular embodiment, the ceramics can include calcium phosphate, hydroxyapatite, calcium sulfate, bioactive glass, or a combination thereof. In an alternative embodiment, the injectable biocompatible materials can include one or more fluids such as sterile water, saline, or sterile air.

Referring back to FIG. 6 and FIG. 7, the expandable interspinous process implant 600 can include one or more bands 606 there around. The bands 606 can be integrally formed with the body 602. Alternatively, the bands 606 can be disposed on an outer surface of the body 602. In a particular embodiment, the bands 606 can reinforce the body 602. Further, the bands 606 can confine the body 602 and prevent the body 602 from expanding radially.

Figure 8:
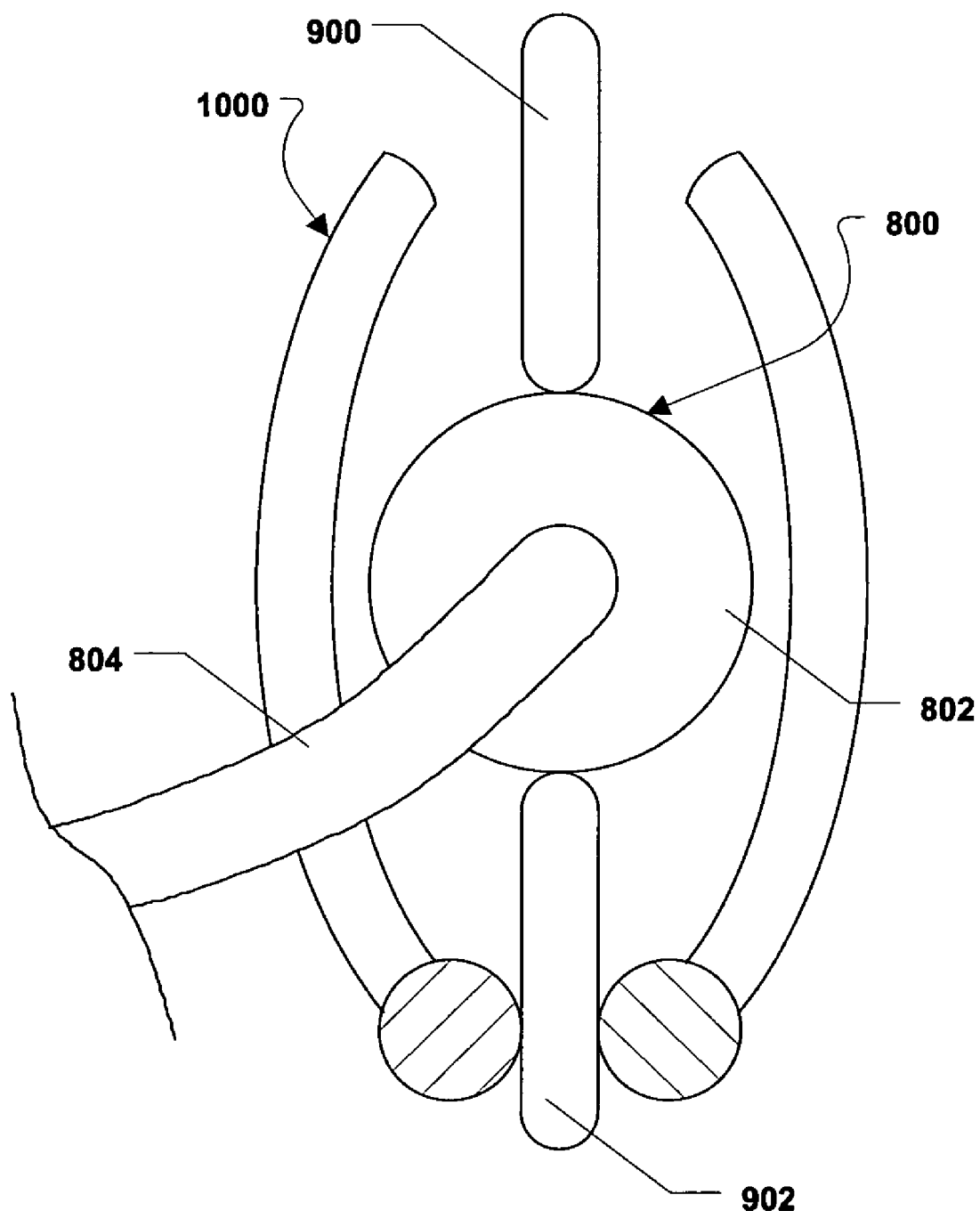
FIG. 8 is a view of an expandable interspinous process implant in a relaxed configuration between adjacent spinous processes and within a first molding device.
Figure 9:
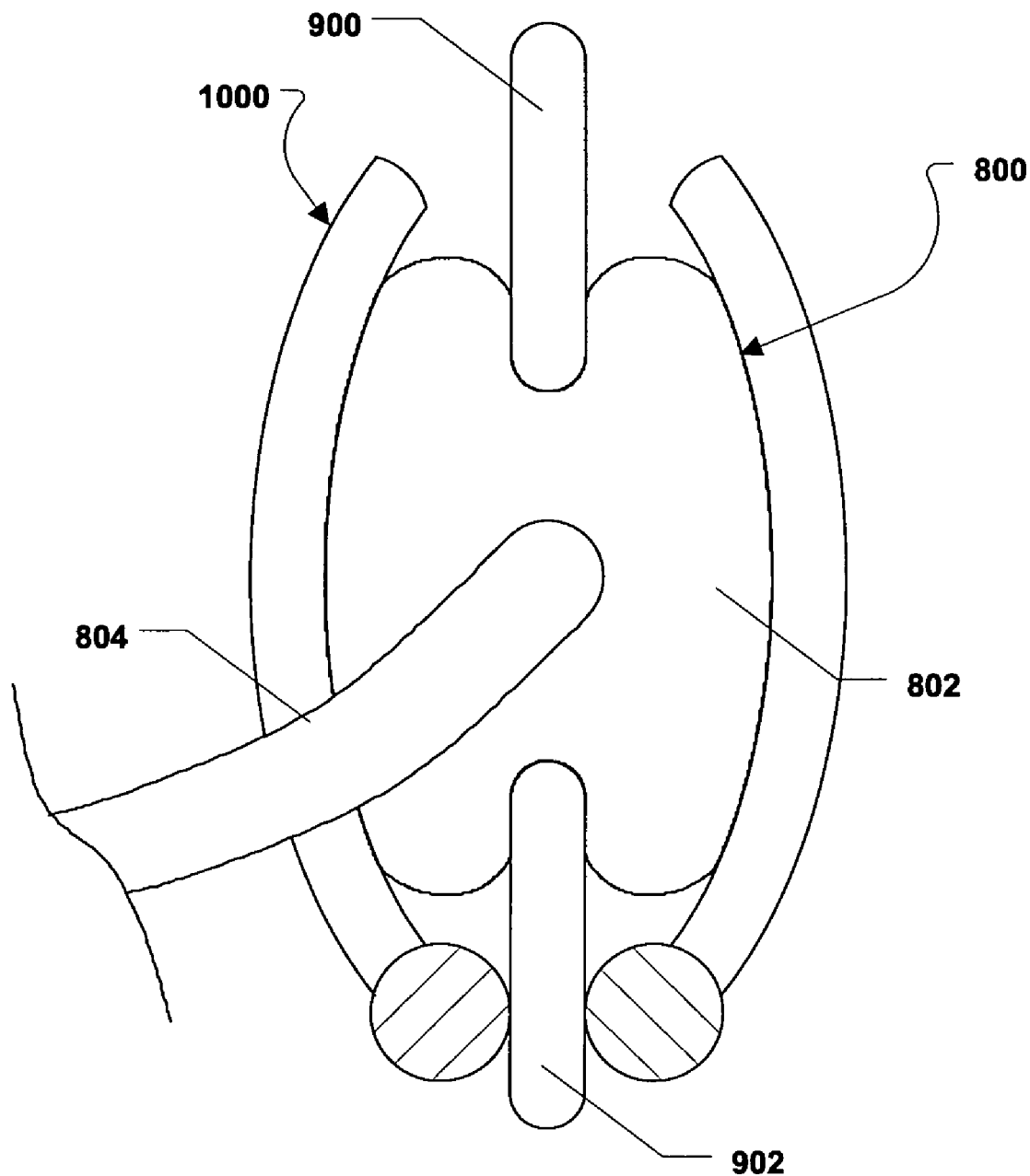
FIG. 9 is a view of the expandable interspinous process implant in an expanded, molded configuration between adjacent spinous processes and within the first molding device.
Figure 10:
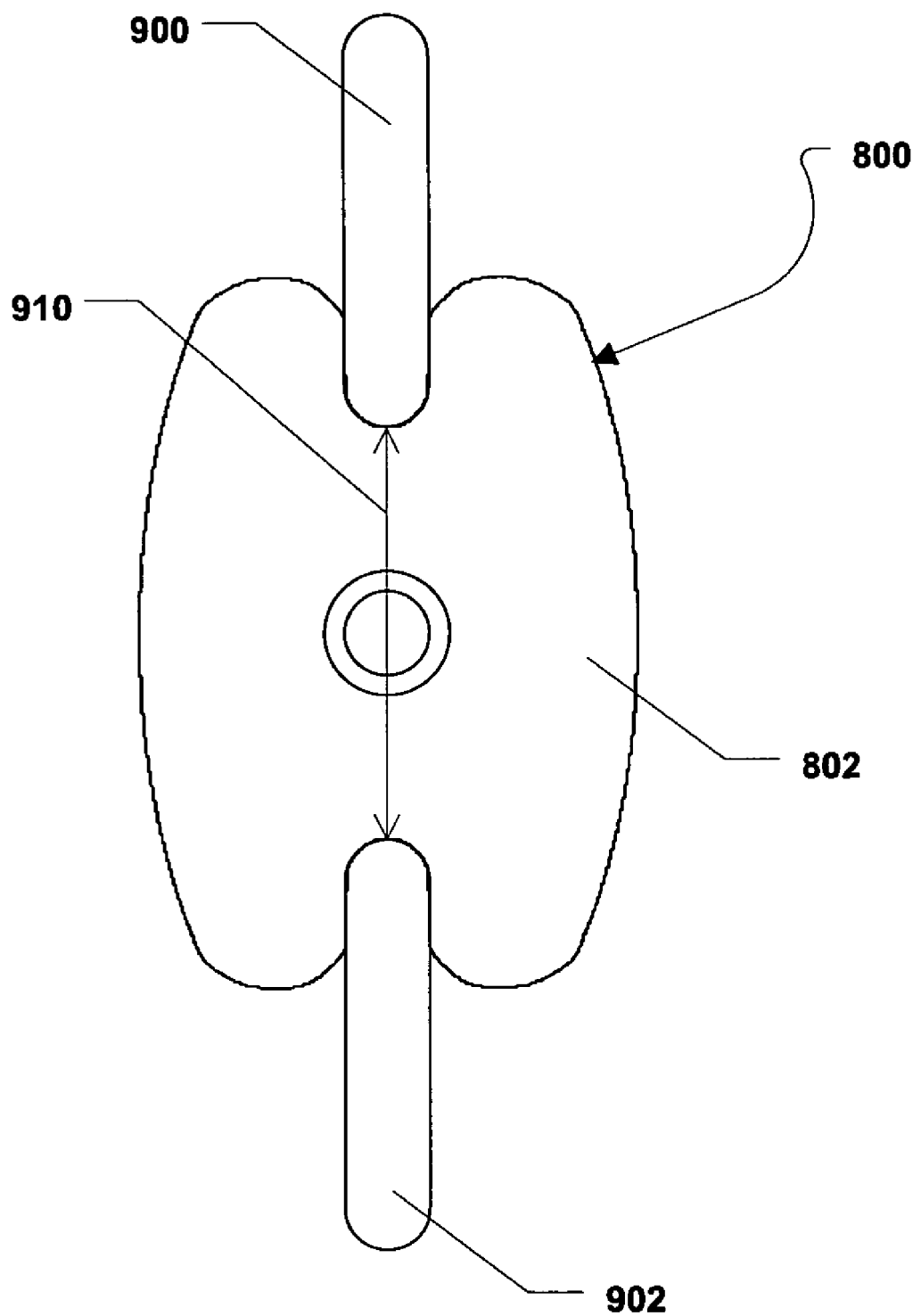
FIG. 10 is a view of the expandable interspinous process implant in an expanded, molded configuration between adjacent spinous processes.

Description of an Expandable Interspinous Process Implant Installed between Adjacent Spinous Processes and within a First Molding Device As shown in FIG. 8 through FIG. 10, an expandable interspinous process implant 800, having a body 802 and an injection tube 804, can be installed between a superior spinous process 900 and an inferior spinous process 902. In a particular embodiment, the expandable interspinous process implant 800 is an expandable interspinous process implant 800 according to one or more embodiments described herein.

As depicted in FIG. 8 and FIG. 9, a molding device 1000 can be placed around the expandable interspinous process implant 800 and the spinous processes 900, 902. Further, the expandable interspinous process implant 800 can be inflated with an injectable biocompatible material, e.g., one or more of the materials described herein. Accordingly, the expandable interspinous process implant 800 can be moved from a relaxed configuration, shown in FIG. 8, to an expanded, molded configuration, shown in FIG. 9 and FIG. 10. In the expanded, molded configuration, the expandable interspinous process implant 800 can substantially conform to a volume bound by the molding device 1000 and the spinous processes 900, 902. Further, in the expanded, molded configuration the expandable interspinous process implant 800, e.g., the body 802, can be partially inflated around the spinous processes 900, 902.

After the expandable interspinous process implant 800 is injected with the injectable biocompatible material, the injectable biocompatible material can be cured and the injection tube 804 and the molding device 1000 can be removed, as shown in FIG. 10. As depicted in FIG. 10, the expandable interspinous process implant 800 can provide support for the spinous processes 900, 902 and prevent a distance 910 between the spinous processes 900, 902 from substantially decreasing—other than slight temporary decreases due to the elasticity of the cured biocompatible material within the expandable interspinous process implant 800.

In another embodiment, a distractor can be used to increase the distance between the superior spinous process 900 and the inferior spinous process 902 and the expandable interspinous process implant 800 can be expanded within the distracted superior spinous process 902 and the inferior spinous process 900. After the expandable interspinous process implant 800 is inflated and cured as described herein, the distractor can be removed and the expandable interspinous process implant 800 can support the superior spinous process 900 and the inferior spinous process 902 and substantially prevent the distance 910 between the superior spinous process 900 and the inferior spinous process 902 from returning to a pre-distraction value.

Description of an Expandable Interspinous Process Implant Installed between Adjacent Spinous Processes and within a Second Molding Device As shown in FIG. 11 through FIG. 14, an expandable interspinous process implant 1100, having a body 1102 and an injection tube 1104, can be installed between a superior spinous process 1200 and an inferior spinous process 1202. In a particular embodiment, the expandable interspinous process implant 1100 is an expandable interspinous process implant 1100 according to one or more embodiments described herein.

Figure 12:
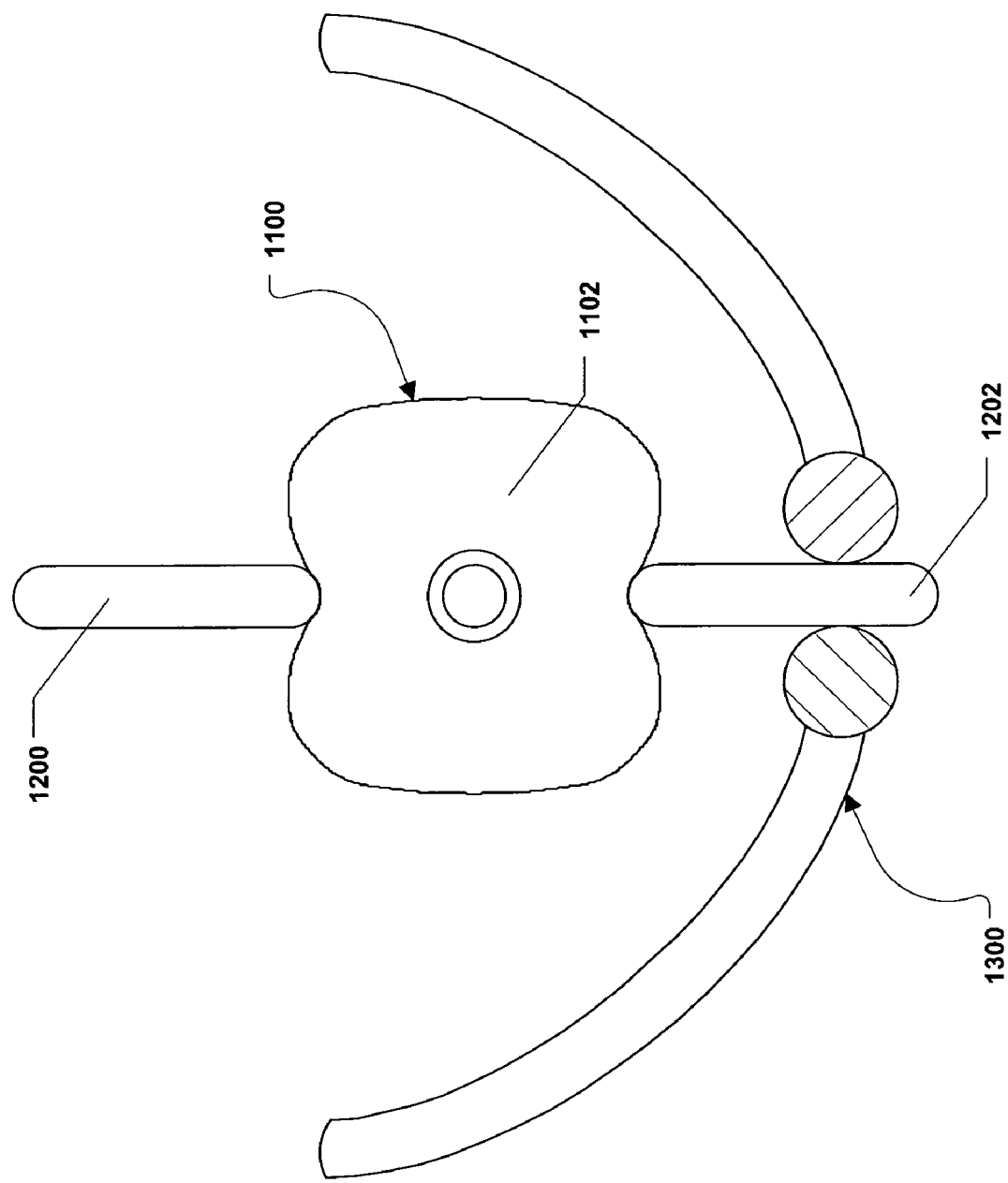
FIG. 12 is a view of the expandable interspinous process implant in an expanded, unmolded configuration between adjacent spinous processes and within a second molding device.
Figure 13:
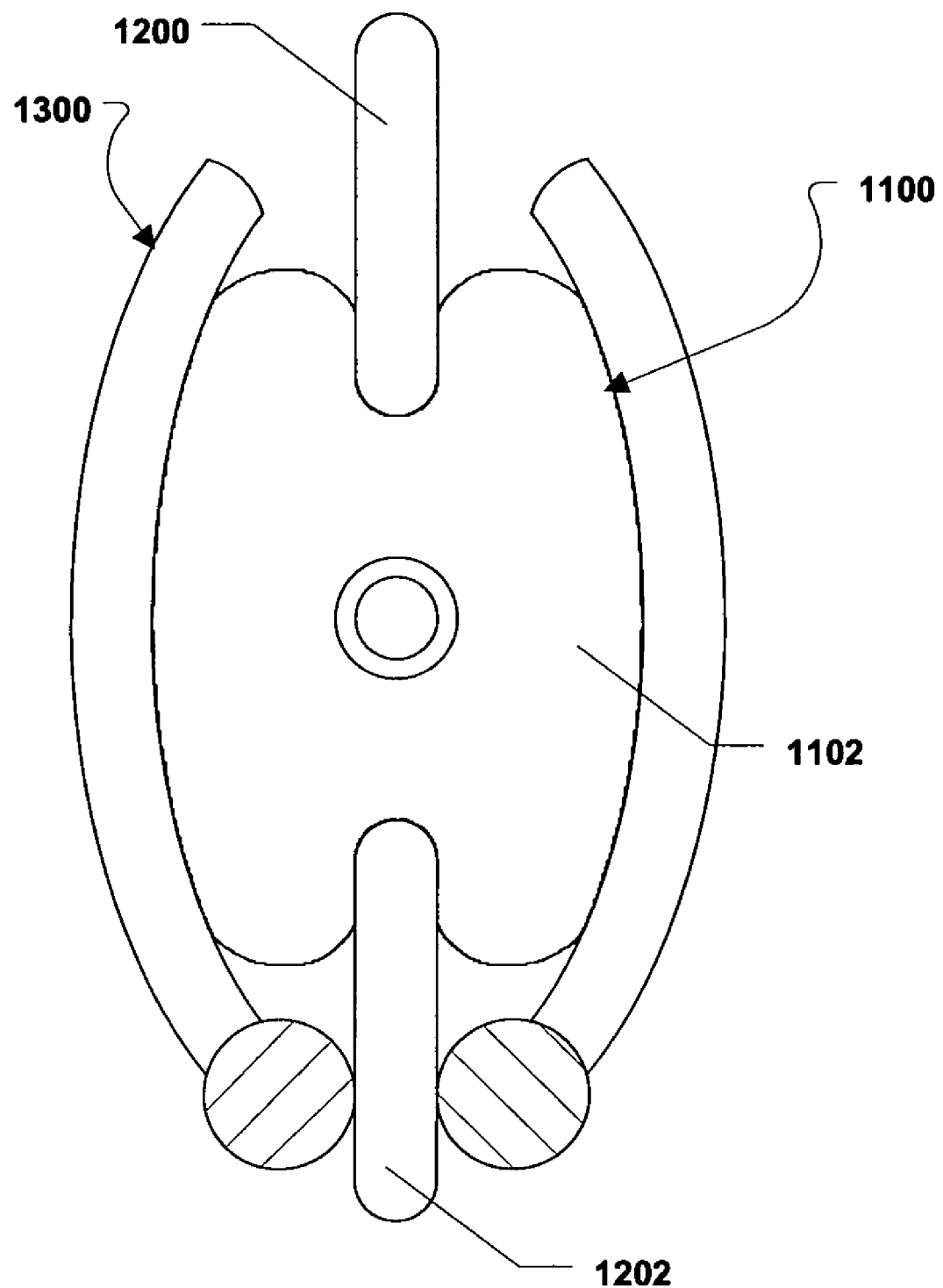
FIG. 13 is a view of the expandable interspinous process implant in an expanded, molded configuration between adjacent spinous processes and within the second molding device.

FIG. 12 illustrates that the expandable interspinous process implant 1100 can be inflated between the superior spinous process 1200 and the inferior spinous process 1202. For example, the expandable interspinous process implant 1100 can be inflated with an injectable biocompatible material, e.g., one or more of the materials described herein.

After the expandable interspinous process implant 1100 is inflated between the spinous processes 1200, 1202, the injection tube 1104 can be removed and a molding device 1300 can be placed around the expandable interspinous process implant 1100 and the spinous processes 1200, 1202. The molding device 1300 can be moved between an open position, shown in FIG. 12, and a closed position, shown in FIG. 13. In the closed position, the molding device 1300 can cause the expandable interspinous process implant 1100 to substantially conform to the area bound by the molding device 1300 and the spinous processes 1200, 1202.

Figure 11:
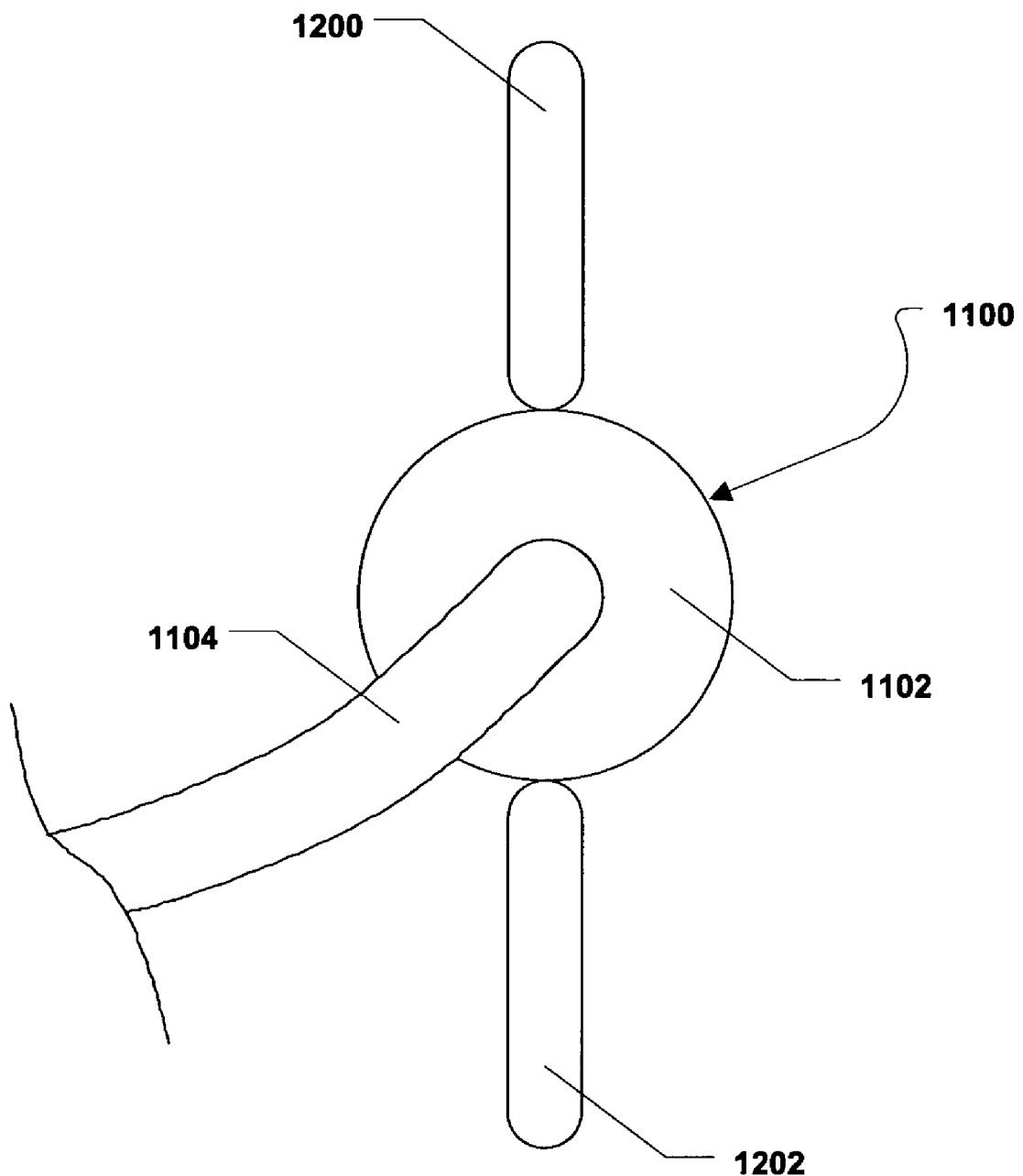
FIG. 11 is a view of an expandable interspinous process implant in a relaxed configuration between adjacent spinous processes.

Accordingly, the expandable interspinous process implant 1100 can be moved from a relaxed configuration, shown in FIG. 11, to an expanded, unmolded configuration, shown in FIG. 12. Further, the expandable interspinous process implant 1100 can be moved from the expanded, unmolded configuration to an expanded, molded configuration. In the expanded, molded configuration, the expandable interspinous process implant 1100 can substantially conform to a volume bound by the molding device 1300 and the spinous processes 1200, 1202. Further, in the expanded, molded configuration the expandable interspinous process implant 1100, e.g., the body 1102, can be partially inflated around the spinous processes 1200, 1202.

Figure 14:
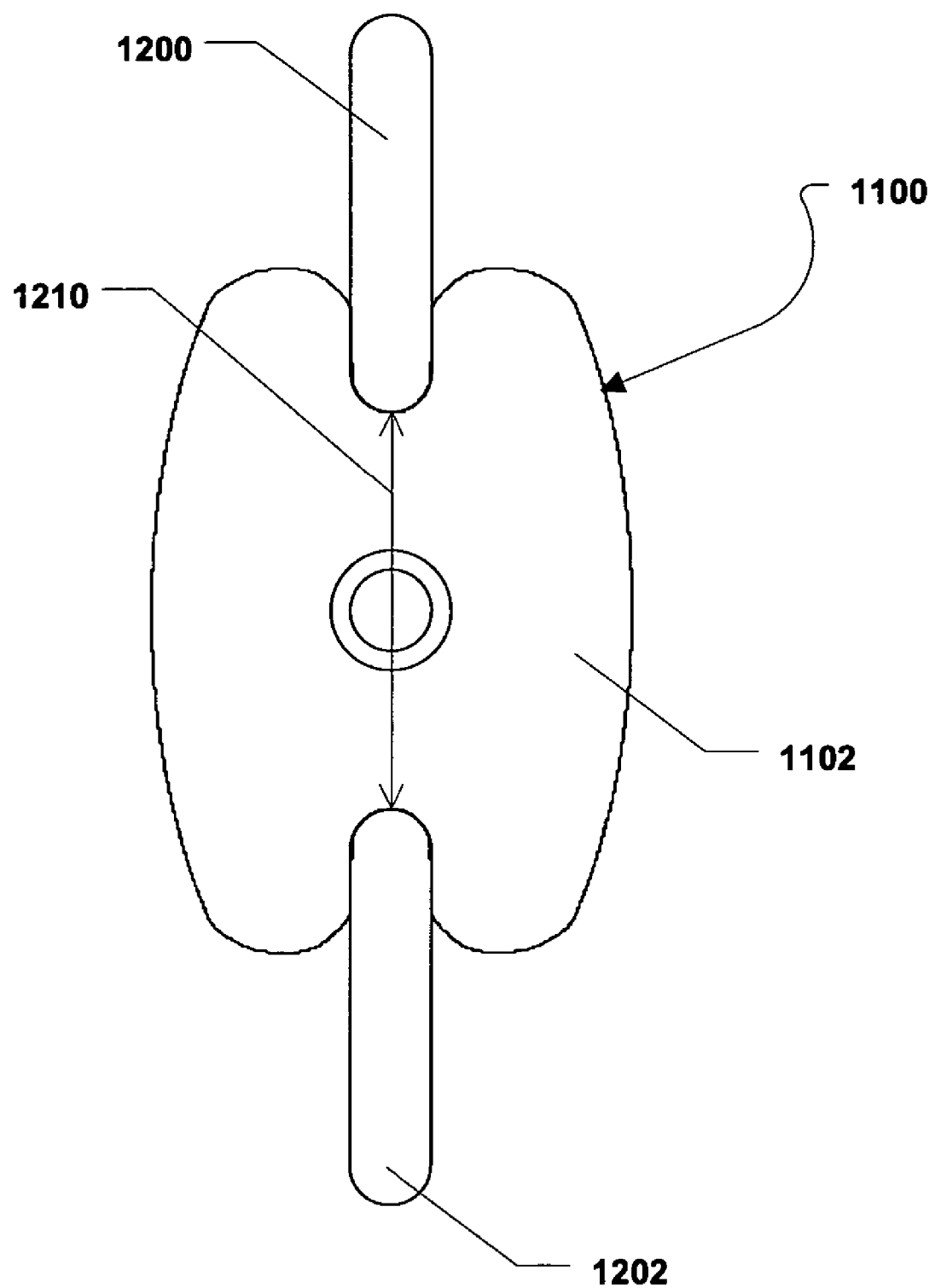
FIG. 14 is a view of the expandable interspinous process implant in an expanded, molded configuration between adjacent spinous processes.
Figure 15:
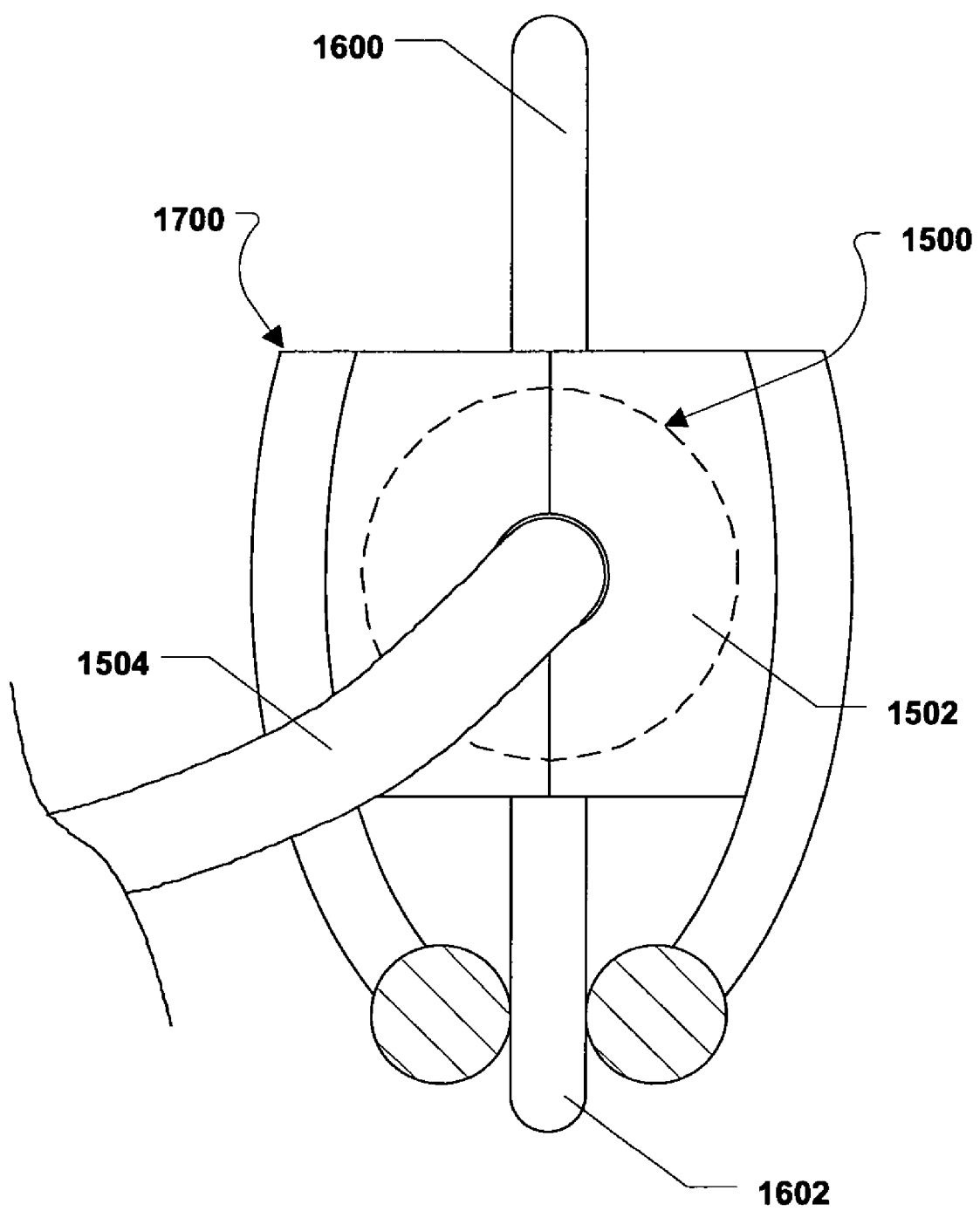
FIG. 15 is a view of an expandable interspinous process implant in a relaxed configuration between adjacent spinous processes and within a third molding device.
Figure 16:
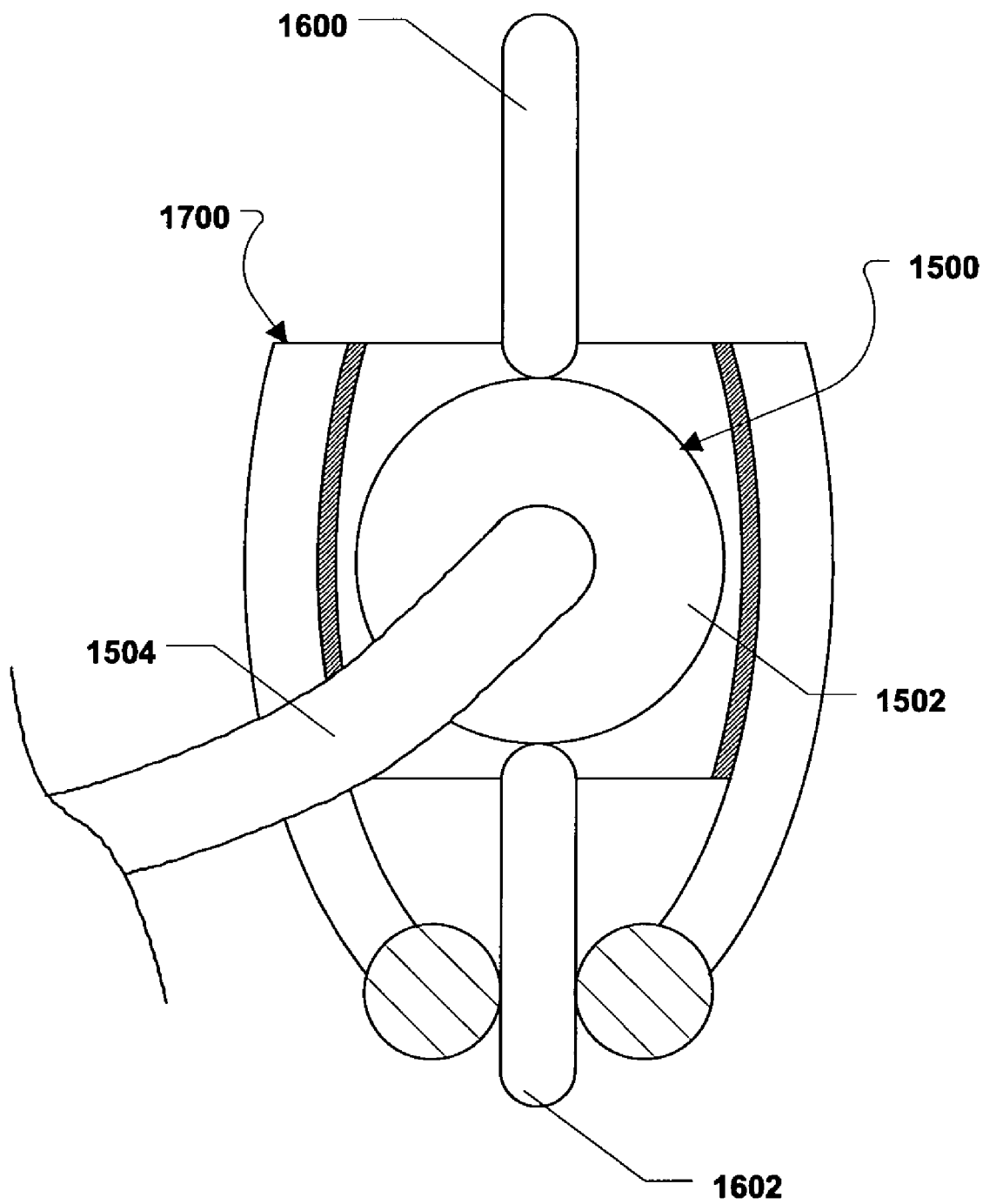
FIG. 16 is a view of an expandable interspinous process implant in a relaxed configuration between adjacent spinous processes and within a third molding device, shown in cross-section.
Figure 17:
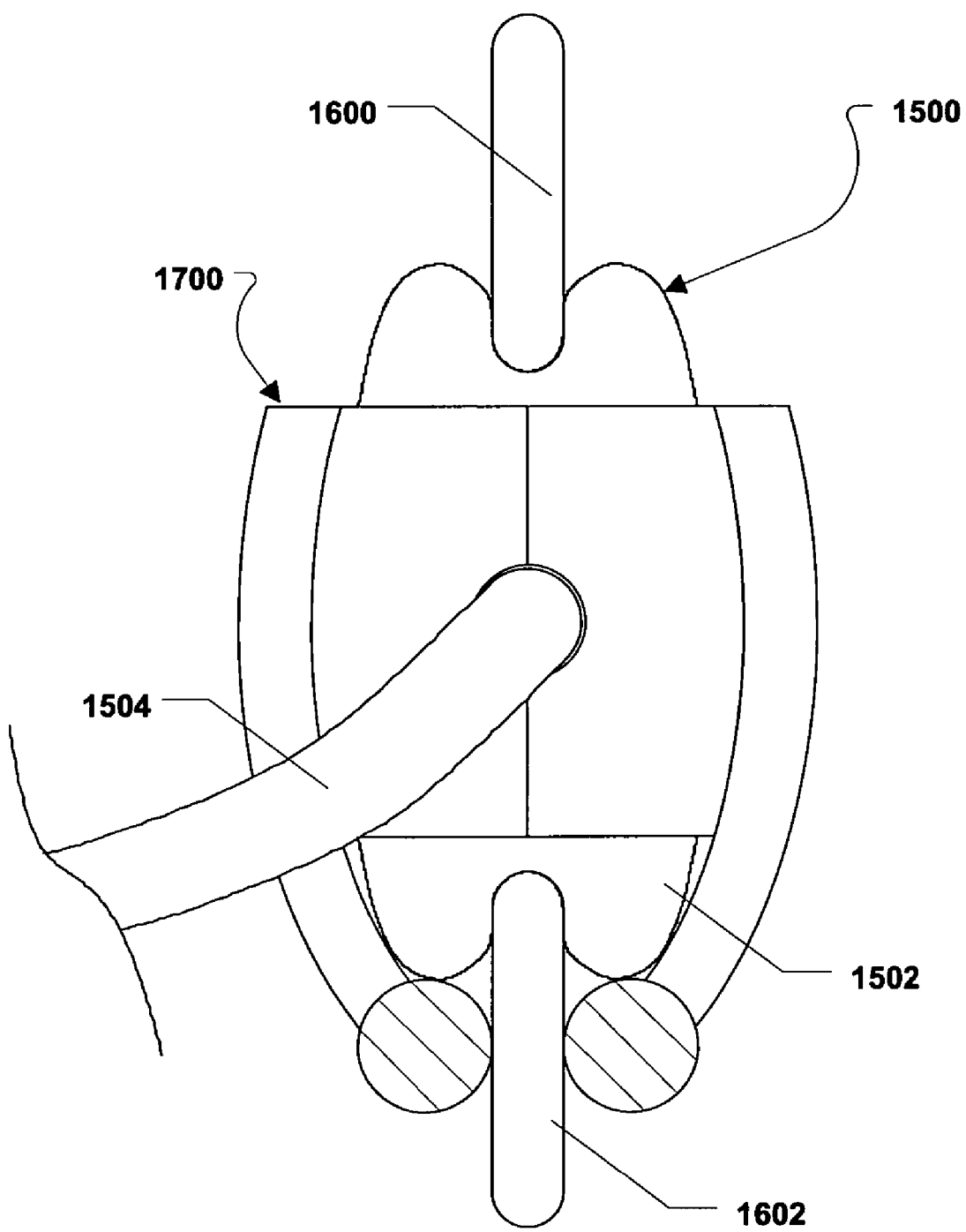
FIG. 17 is a view of the expandable interspinous process implant in an expanded, molded configuration between adjacent spinous processes and within the third molding device.
Figure 18:
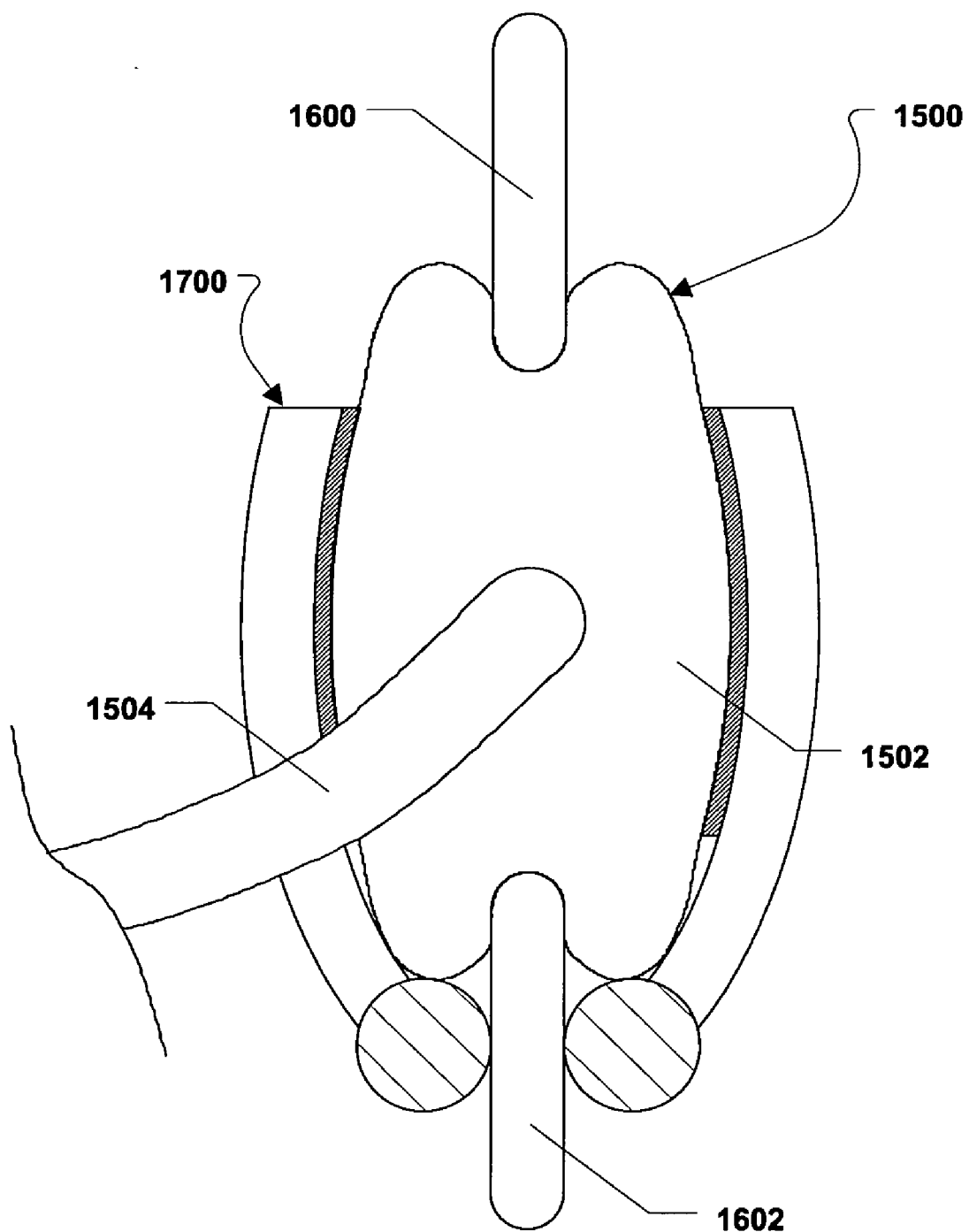
FIG. 18 is a view of the expandable interspinous process implant in an expanded, molded configuration between adjacent spinous processes and within the third molding device, shown in cross-section.

After the expandable interspinous process implant 1100 is injected with the injectable biocompatible material and molded as described herein, the injectable biocompatible material can be cured and the molding device 1300 can be removed, as shown in FIG. 14. In various embodiments, the injectable biocompatible material can be cured by application of an energy source or by chemical activation or in any art-recognized manner appropriate to the material used. In certain embodiments, the injection tube can be retained in place after injection in order to provide a conduit for delivering a curing agent into the body.

As depicted in FIG. 14, the expandable interspinous process implant 1100 can provide support for the spinous processes 1200, 1202 and substantially prevent a distance 1210 between the spinous processes 1200, 1202 from decreasing—other than slight temporary decreases due to the elasticity of the cured biocompatible material within the expandable interspinous process implant 800.

In another embodiment, a distractor can be used to increase the distance between the superior spinous process 1200 and the inferior spinous process 1202 and the expandable interspinous process implant 1100 can be expanded within the distracted superior spinous process 1202 and the inferior spinous process 1200. After the expandable interspinous process implant 1100 is inflated, molded, and cured as described herein, the distractor can be removed and the expandable interspinous process implant 1100 can support the superior spinous process 1200 and the inferior spinous process 1202 and substantially prevent the distance 1210 between the superior spinous process 1200 and the inferior spinous process 1202 from returning to a pre-distraction value.

Description of an Expandable Interspinous Process Implant Installed between Adjacent Spinous Processes and within a Third Molding Device As shown in FIG. 15 through FIG. 19, an expandable interspinous process implant 1500, having a body 1502 and an injection tube 1504, can be installed between a superior spinous process 1600 and an inferior spinous process 1602. In a particular embodiment, the expandable interspinous process implant 1500 is an expandable interspinous process implant 1500 according to one or more embodiments described herein.

As depicted in FIG. 15 through FIG. 18, a molding device 1700 can be placed around the expandable interspinous process implant 1500 and the spinous processes 1600, 1602. Further, the expandable interspinous process implant 1500 can be inflated with an injectable biocompatible material, e.g., one or more of the materials described herein. Accordingly, the expandable interspinous process implant 1500 can be moved from a relaxed configuration, shown in FIG. 15 and FIG. 16, to an expanded, molded configuration, shown in FIG. 17 through FIG. 19. As the expandable interspinous process implant 1500 expands, it can distract the spinous processes 1600, 1602 and increase a distance 1610 therebetween. Further, in the expanded, molded configuration, the expandable interspinous process implant 1500 can substantially conform to a volume bound by the molding device 1700 and the spinous processes 1600, 1602. Further, in the expanded, molded configuration the expandable interspinous process implant 1500, e.g., the body 1502, can be partially inflated around the spinous processes 1600, 1602.

Figure 19:
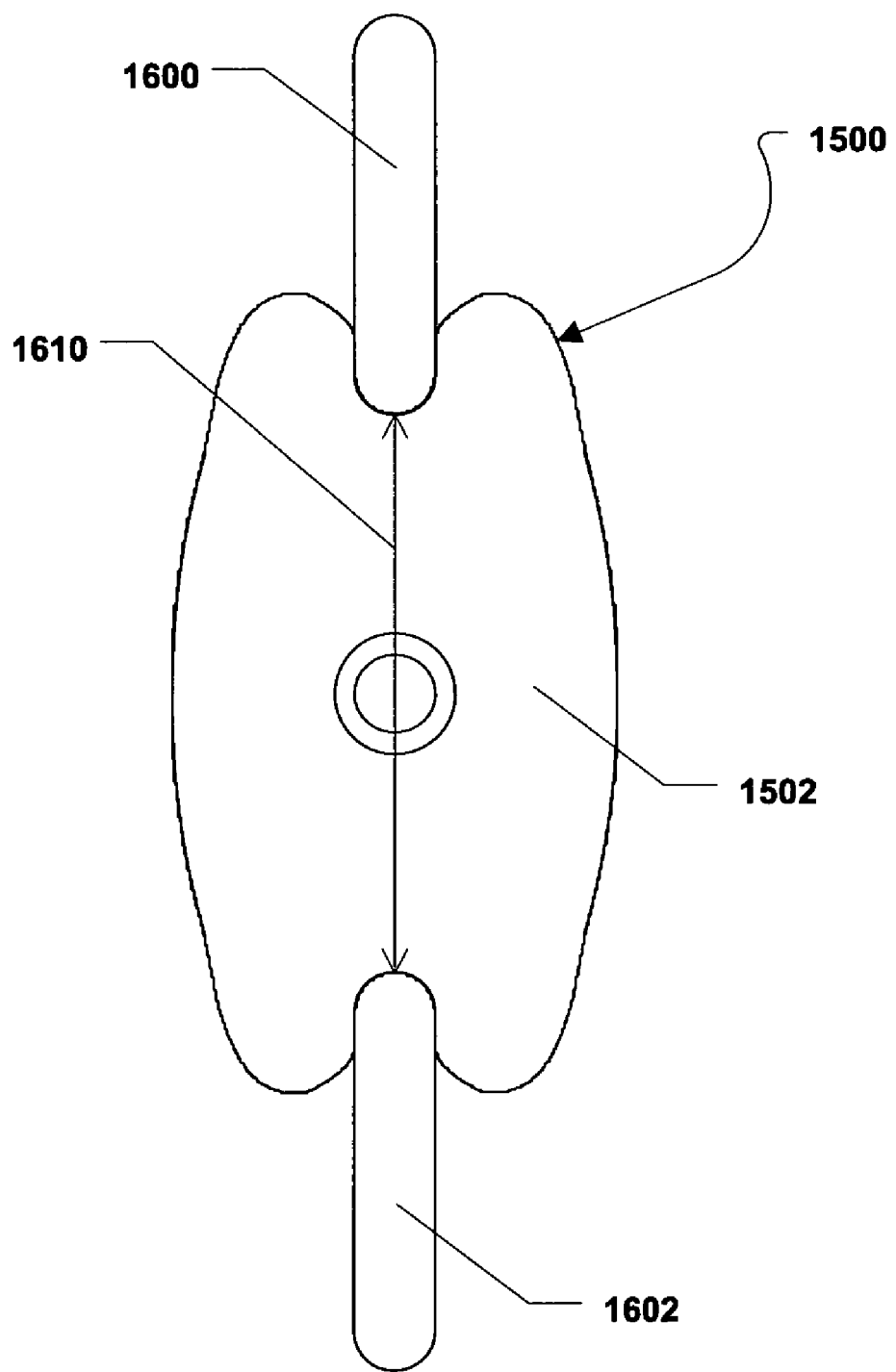
FIG. 19 is a view of the expandable interspinous process implant in an expanded, molded configuration between adjacent spinous processes.

After the expandable interspinous process implant 1500 is injected with the injectable biocompatible material, the injectable biocompatible material can be cured and the injection tube 1504 and the molding device 1700 can be removed, as shown in FIG. 19. As depicted in FIG. 19, the expandable interspinous process implant 1500 can provide support for the spinous processes 1600, 1602 and prevent the distance 1610 between the spinous processes 1600, 1602 from substantially decreasing—other than slight temporary decreases due to the elasticity of the cured biocompatible material within the expandable interspinous process implant 1500.

In another embodiment, a distractor can be used to increase the distance between the superior spinous process 1600 and the inferior spinous process 1602 and the expandable interspinous process implant 1500 can be expanded within the distracted superior spinous process 1602 and the inferior spinous process 1600. After the expandable interspinous process implant 1500 is inflated and cured as described herein, the distractor can be removed and the expandable interspinous process implant 1500 can support the superior spinous process 1600 and the inferior spinous process 1602 and substantially prevent the distance 1610 between the superior spinous process 1600 and the inferior spinous process 1602 from returning to a pre-distraction value.

Description of a First Molding Device

Referring now to FIG. 20 through FIG. 23, a first embodiment of a molding device is shown and is generally designated 2000. As shown, the molding device 2000 includes a body 2002 that can include a proximal end 2004 and a distal end 2006. A handle 2008 can be attached to the proximal end 2004 of the body 2002.

Figure 20:
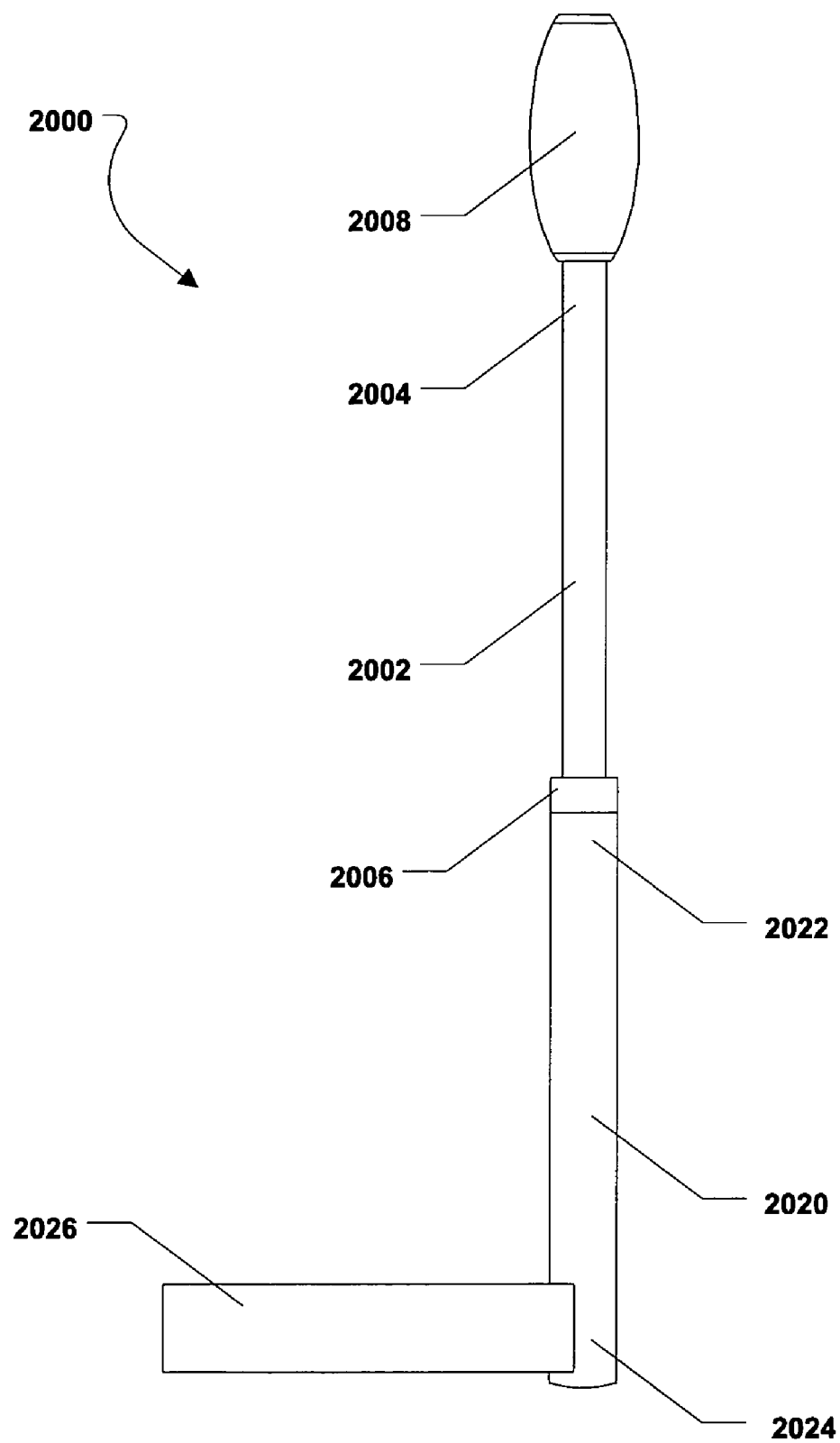
FIG. 20 is a side plan view of a first molding device.
Figure 21:
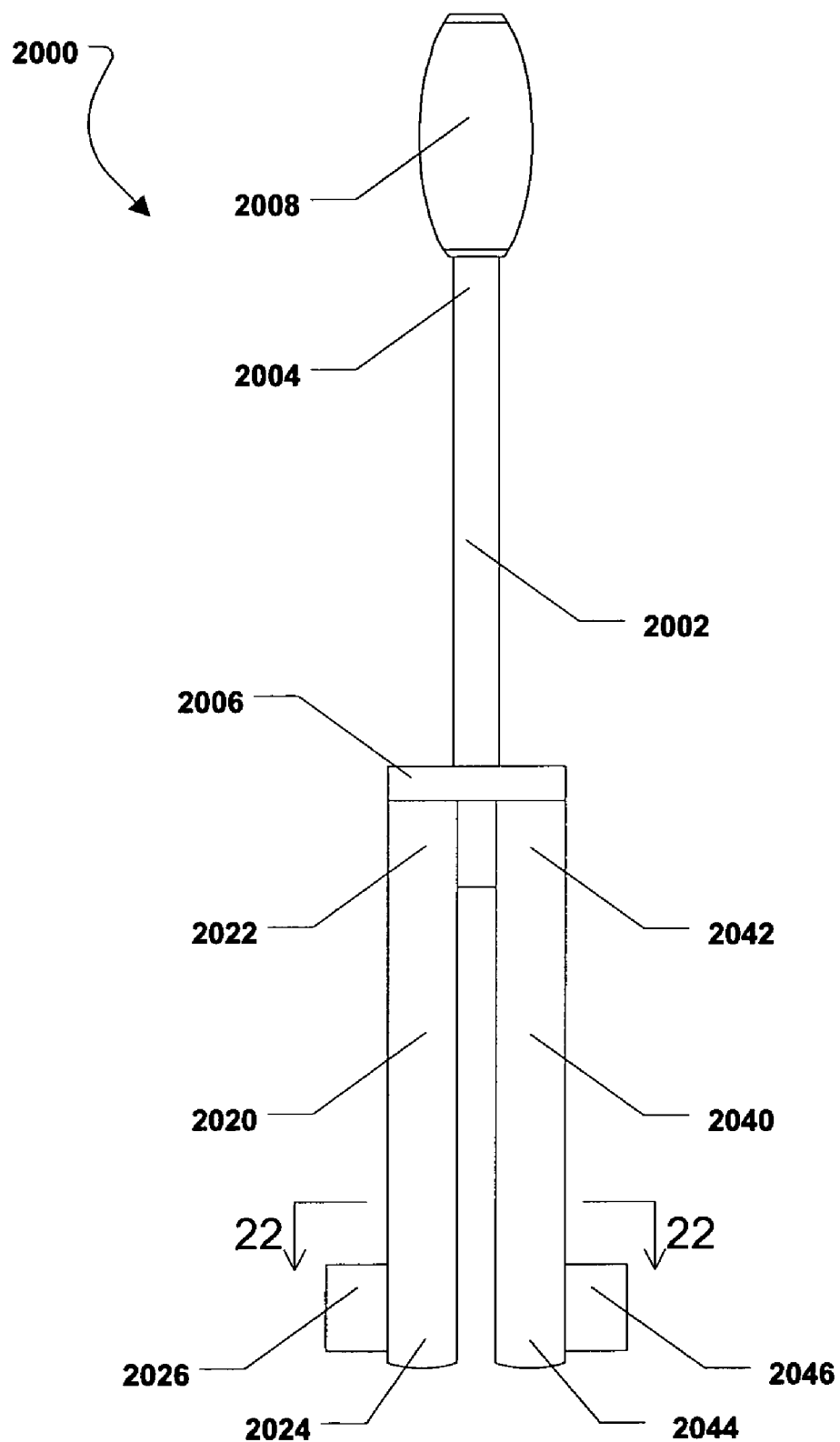
FIG. 21 is rear plan view of the first molding device.

FIG. 20 and FIG. 21 indicate that a first support post 2020 can extend from the distal end 2006 of the body 2002. Specifically, the first support post 2020 can include a proximal end 2022 and a distal end 2024 and the proximal end 2022 of the first support post 2020 can be connected, or otherwise attached, to the distal end 2006 of the body 2002.

Figure 22:
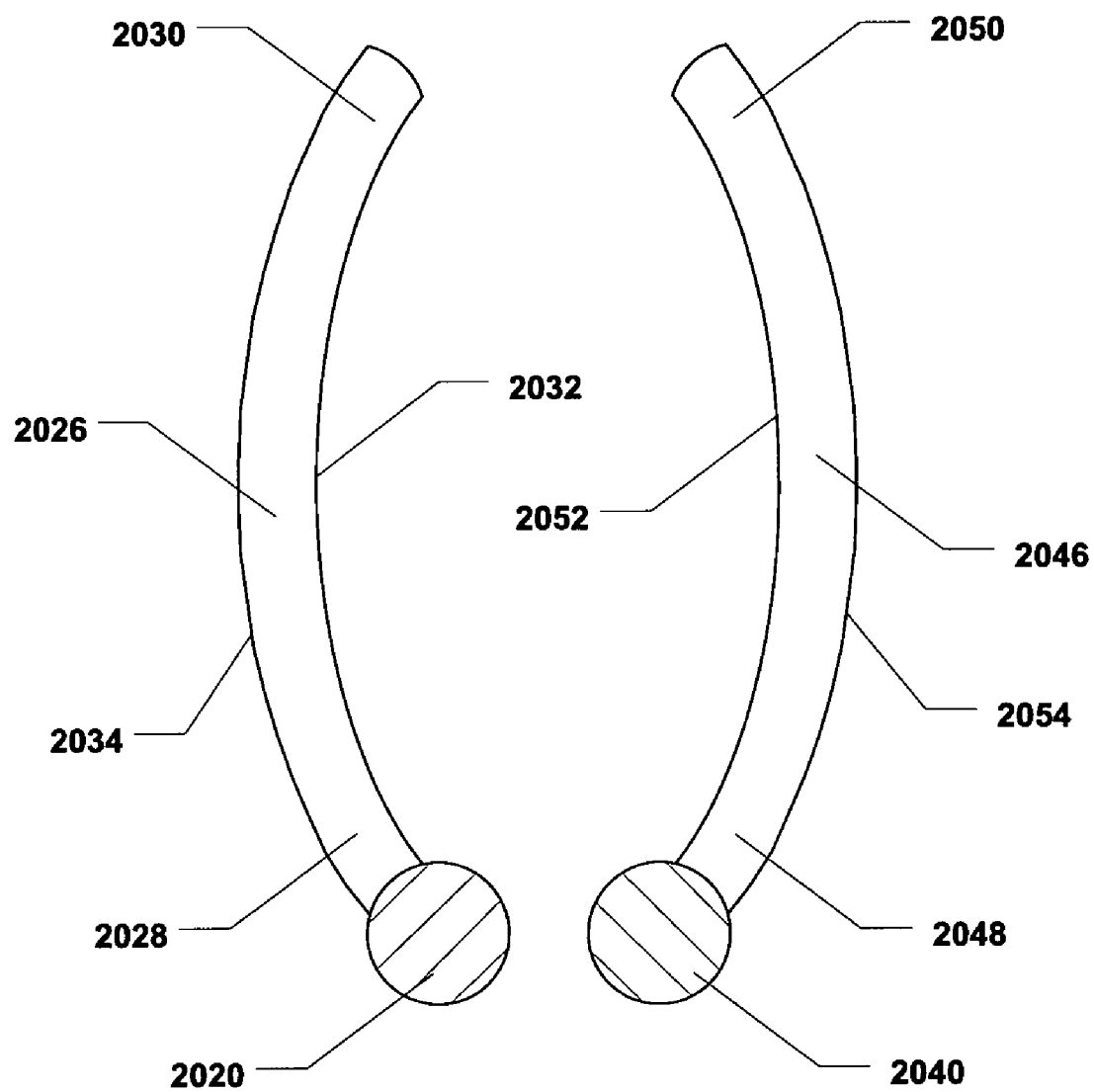
FIG. 22 is a cross-section view of the first molding device taken along line 22-22 in FIG. 21.

Moreover, a first mold component 2026 can be attached to, or otherwise extend from, the distal end 2024 of the first support post 2020. As shown in FIG. 22, the first mold component 2026 can include a proximal end 2028 and a distal end 2030. The first mold component 2026 can also include an interior surface 2032 and an exterior surface 2034.

FIG. 20 and FIG. 21 indicate that a second support post 2040 can extend from the distal end 2006 of the body 2002. Specifically, the second support post 2040 can include a proximal end 2042 and a distal end 2044 and the proximal end 2042 of the second support post 2040 can be connected, or otherwise attached, to the distal end 2006 of the body 2002.

Moreover, a second mold component 2046 can be attached to, or otherwise extend from, the distal end 2044 of the second support post 2040. As shown in FIG. 22, the second mold component 2046 can include a proximal end 2048 and a distal end 2050. The second mold component 2046 can also include an interior surface 2052 and an exterior surface 2054.

Figure 23:
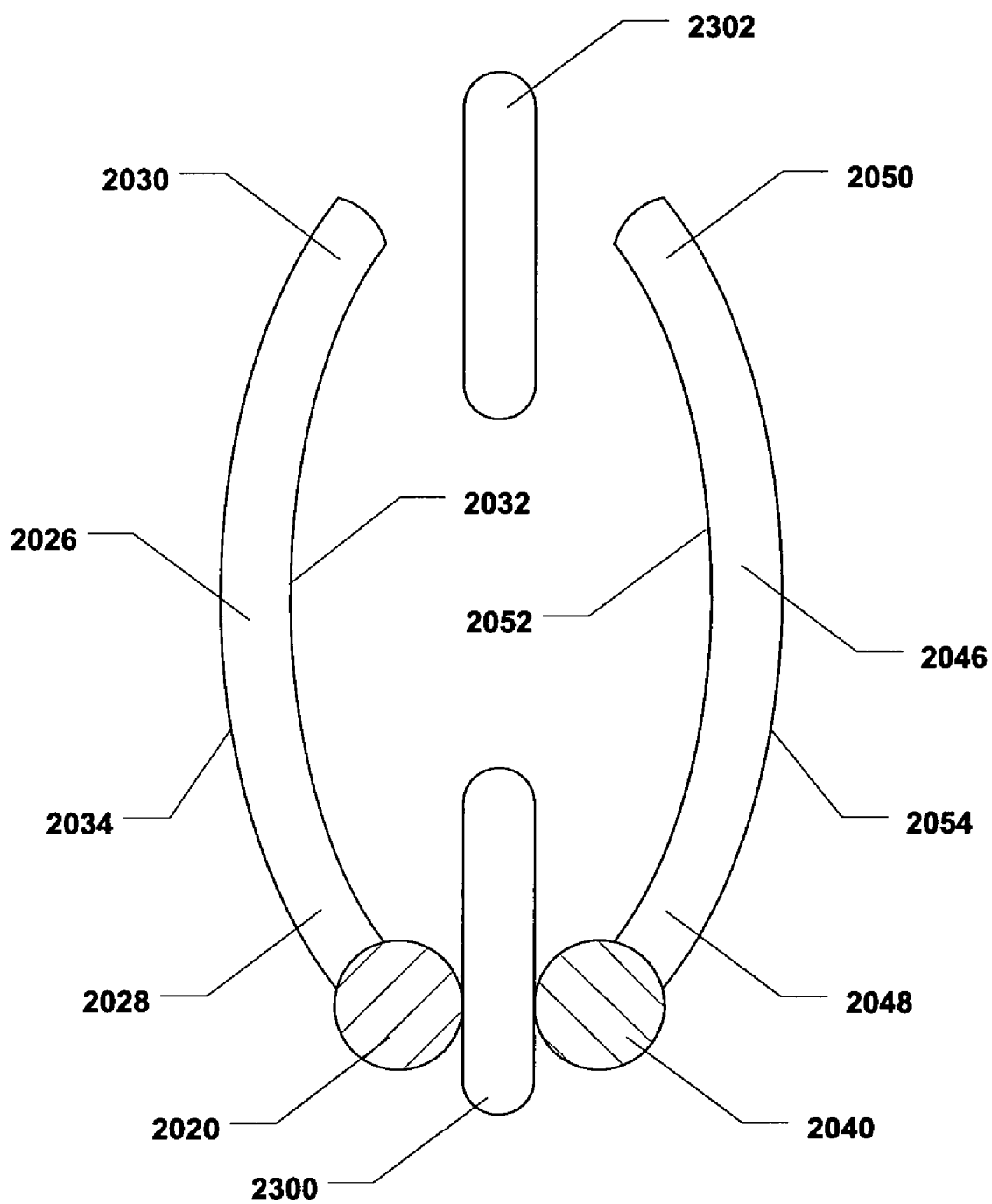
FIG. 23 is a cross-section view of the first molding device installed around adjacent spinous processes.

In a particular embodiment, as shown in FIG. 23, the molding device 2000 can be placed around adjacent spinous processes such that the proximal end 2028, 2048 of each mold component 2026, 2046 can be near a first spinous process 2300. Further, the distal end 2030, 2050 of each mold component 2026, 2046 can be near a second spinous process 2302.

As illustrated in FIG. 23, the interior surfaces 2032, 2052 of the mold components 2026, 2046 and the spinous processes 2300, 2302 can create a volume into which an expandable interspinous process implant can be inserted, expanded, and molded, as described herein.

Description of a First Method of Treating a Spine

Figure 24:
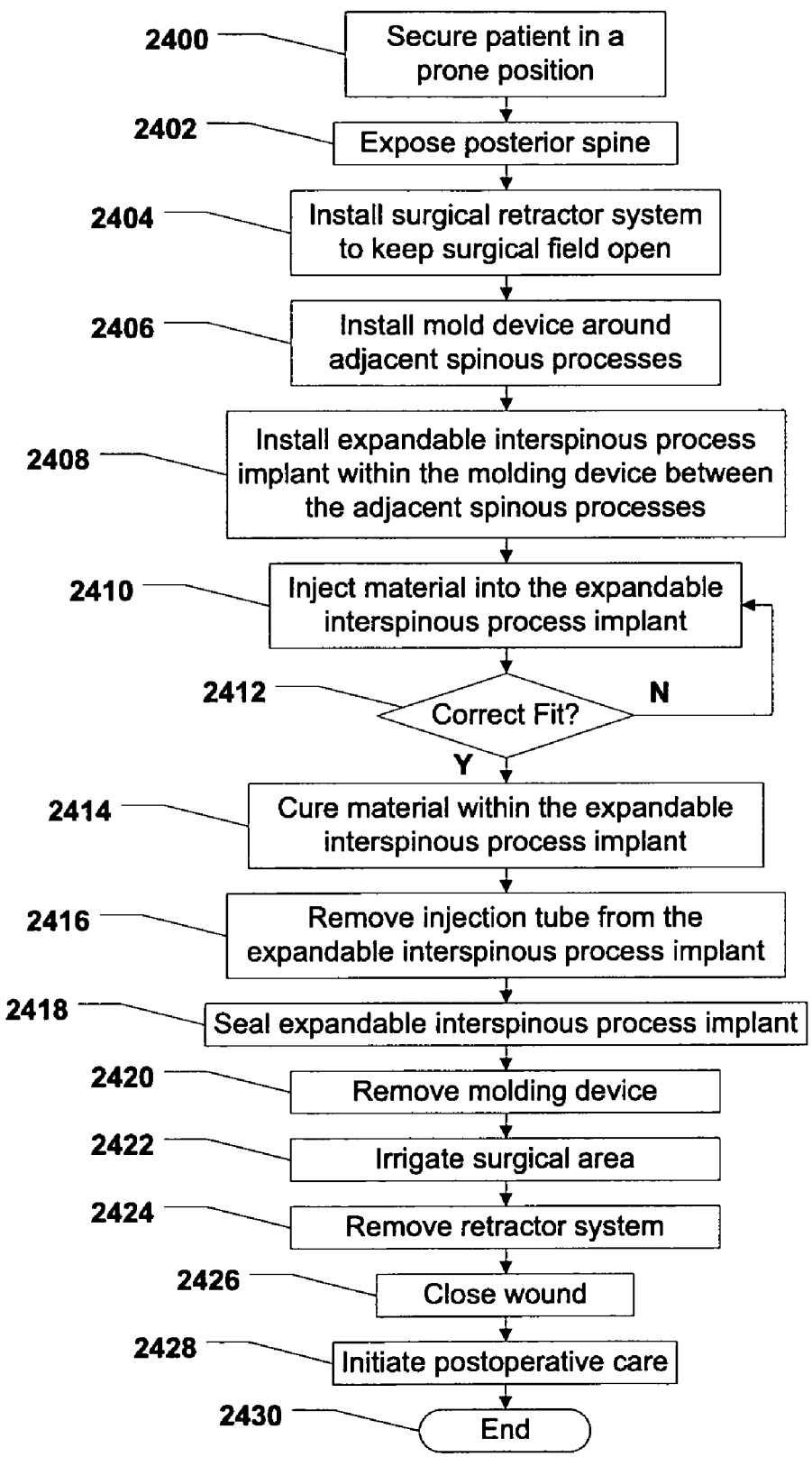
FIG. 24 is a flow chart illustrating a first method of treating a spine.

Referring to FIG. 24, a method of treating a spine is shown and commences at block 2400. At block 2400, a patient can be secured in a prone position, e.g., on an operating table. At block 2402, the posterior spine can be exposed in order to expose adjacent spinous processes. Further, at block 2404, a surgical retractor system can be installed to keep a surgical field open.

Moving to block 2406, a molding device can be inserted around two adjacent spinous processes. In a particular embodiment, the molding device can be a molding device according to one or more of the embodiments described herein. At block 2408, an expandable interspinous process implant can be installed within the molding device between the adjacent spinous processes. In a particular embodiment, the expandable interspinous process implant can be an expandable interspinous process implant according to one or more of the embodiments described herein.

At block 2410, an injectable biocompatible material can be injected into the expandable interspinous process implant. In a particular embodiment, the injectable biocompatible material can be one or more of the materials described herein. Proceeding to decision step 2412, it can be determined whether the fit of the expandable interspinous process implant is correct. In other words, it can be determined whether to inject more material into the expandable interspinous process implant. At decision step 2412, if the fit of the expandable interspinous process implant is not correct, the method returns to block 2410 and more material can be injected into the expandable interspinous process implant. Thereafter, the method can continue as described herein.

Returning to decision step 2412, if the fit of the expandable interspinous process implant is correct, the method can proceed to block 2414 and the material within the expandable interspinous process implant can be cured. In a particular embodiment, the material within the expandable interspinous process implant can cure naturally, i.e., under ambient conditions, in situ. Alternatively, the material within the expandable interspinous process implant can be cured in situ using an energy source. For example, the energy source can be a light source that emits visible light, infrared (IR) light, or ultraviolet (UV) light. Further, the energy source can be a heating device, a radiation device, or other mechanical device.

Moving to block 2416, an injection tube can be removed from the expandable interspinous process implant. Further, at block 2418, the expandable interspinous process implant can be sealed. In a particular embodiment, the expandable interspinous process implant can be sealed by curing the material within the expandable interspinous process implant. Alternatively, a plug, a dowel, or another similar device can be used to seal the expandable interspinous process implant. Further, a one-way valve can be incorporated into the expandable interspinous process implant and can allow material to be injected into the expandable interspinous process implant, but prevent the same material from being expelled from the expandable interspinous process implant.

Continuing to block 2420, the molding device can be removed from around the spinous processes and the expandable interspinous process implant. Thereafter, at block 2422, the surgical area can be irrigated. At block 2424, the retractor system can be removed. Further, at block 2426, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 2428, postoperative care can be initiated. The method can end at state 2430.

In a particular embodiment, the spinous processes can be distracted prior to inserting the molding device and the expandable interspinous process implant. After the expandable interspinous process implant is inflated, molded, and cured as described herein, the distractor can be removed and the expandable interspinous process implant can support the superior spinous process and the inferior spinous process and substantially prevent a distance between the superior spinous process and the inferior spinous process from returning to a pre-distraction value.

Description of a Second Molding Device

Referring now to FIG. 25 through FIG. 28, a second embodiment of a molding device is shown and is generally designated 2500. As shown, the molding device 2500 includes a body 2502 that can include a proximal end 2504 and a distal end 2506. A handle 2508 can be attached to the proximal end 2504 of the body 2502.

Figure 25:
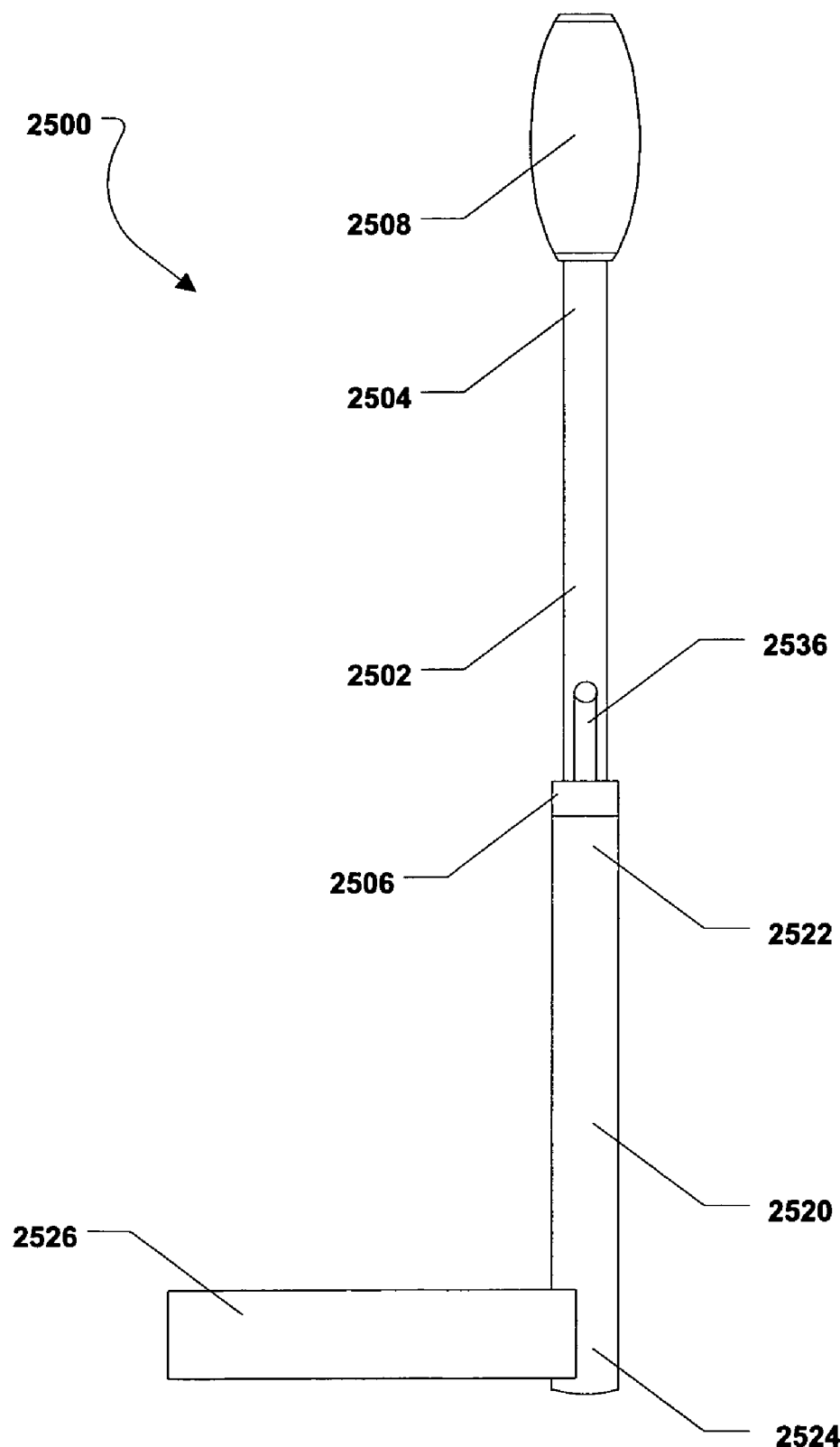
FIG. 25 is a side plan view of a second molding device.
Figure 26:
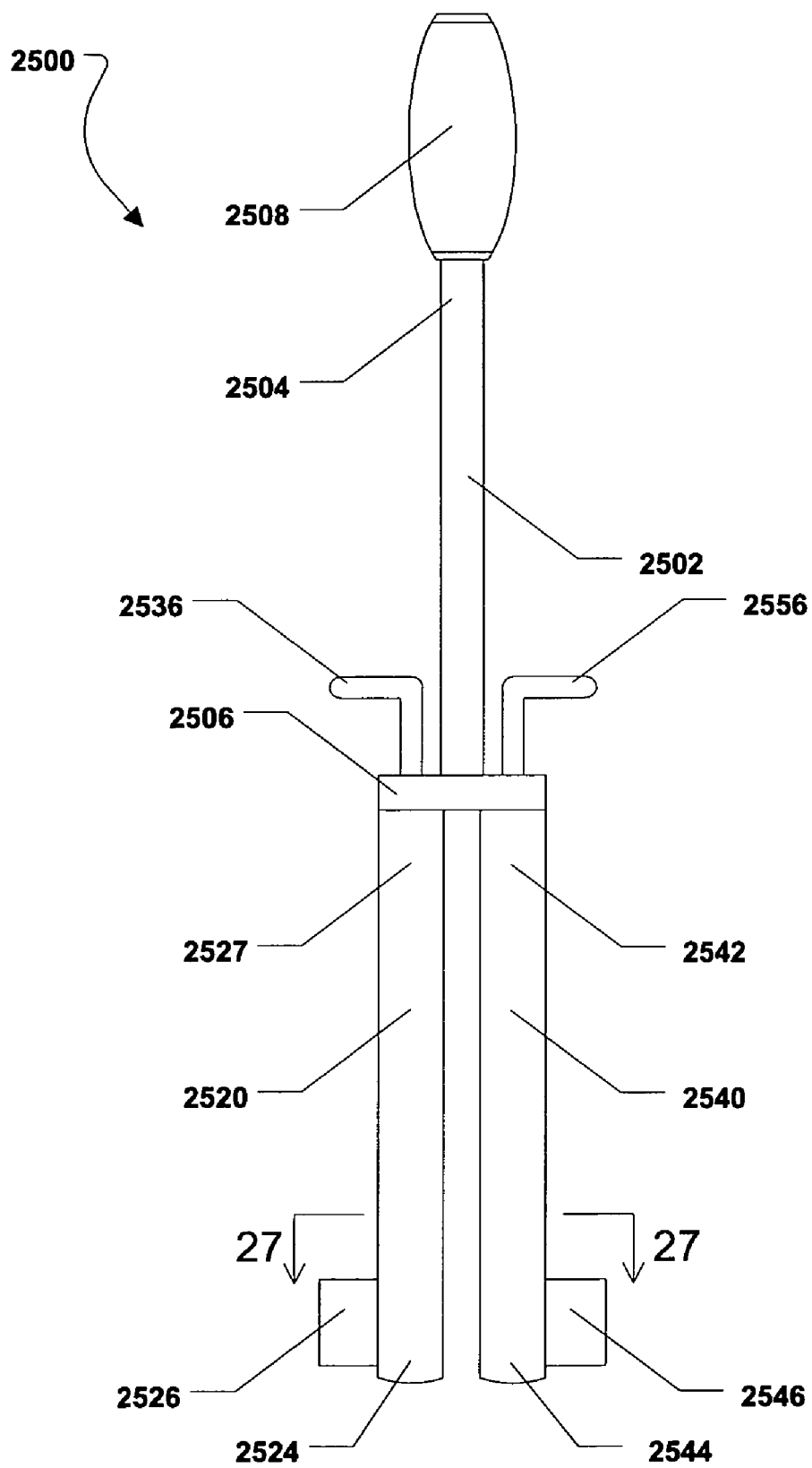
FIG. 26 is rear plan view of the second molding device.

FIG. 25 and FIG. 26 indicate that a first support post 2520 can extend from the distal end 2506 of the body 2502. Specifically, the first support post 2520 can include a proximal end 2522 and a distal end 2524 and the proximal end 2522 of the first support post 2520 can be rotably engaged with the distal end 2506 of the body 2502.

Figure 27:
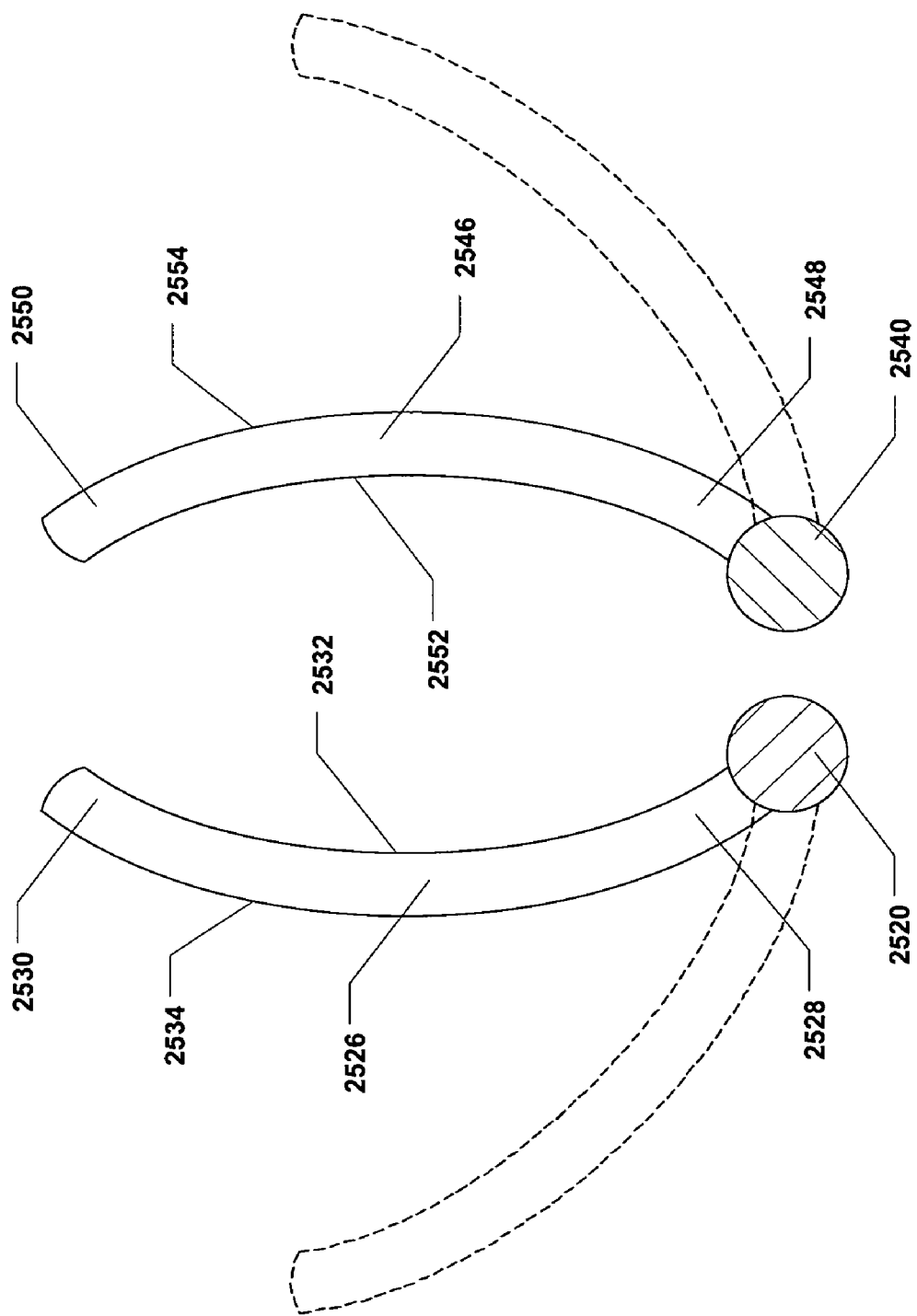
FIG. 27 is a cross-section view of the second molding device taken along line 27-27 in FIG. 26.

Moreover, a first mold component 2526 can be attached to, or otherwise extend from, the distal end 2524 of the first support post 2520. As shown in FIG. 27, the first mold component 2526 can include a proximal end 2528 and a distal end 2530. The first mold component 2526 can also include an interior surface 2532 and an exterior surface 2534.

As shown in FIG. 19 and FIG. 25, a first handle 2536 can extend from the proximal end 2522 of the first support post

2520. The first handle 2536 can be used to rotate the first support post 2520 relative to the body 2502.

FIG. 25 and FIG. 26 indicate that a second support post 2540 can extend from the distal end 2506 of the body 2502. Specifically, the second support post 2540 can include a proximal end 2542 and a distal end 2544 and the proximal end 2542 of the second support post 2540 can be rotably engaged with to the distal end 2506 of the body 2502.

Moreover, a second mold component 2546 can be attached to, or otherwise extend from, the distal end 2544 of the second support post 2540. As shown in FIG. 27, the second mold component 2546 can include a proximal end 2548 and a distal end 2550. The second mold component 2546 can also include an interior surface 2552 and an exterior surface 2554.

As shown in FIG. 19 and FIG. 25, a second handle 2556 can extend from the proximal end 2542 of the first support post 2540. The second handle 2556 can be used to rotate the second support post 2540 relative to the body 2502.

Figure 28:
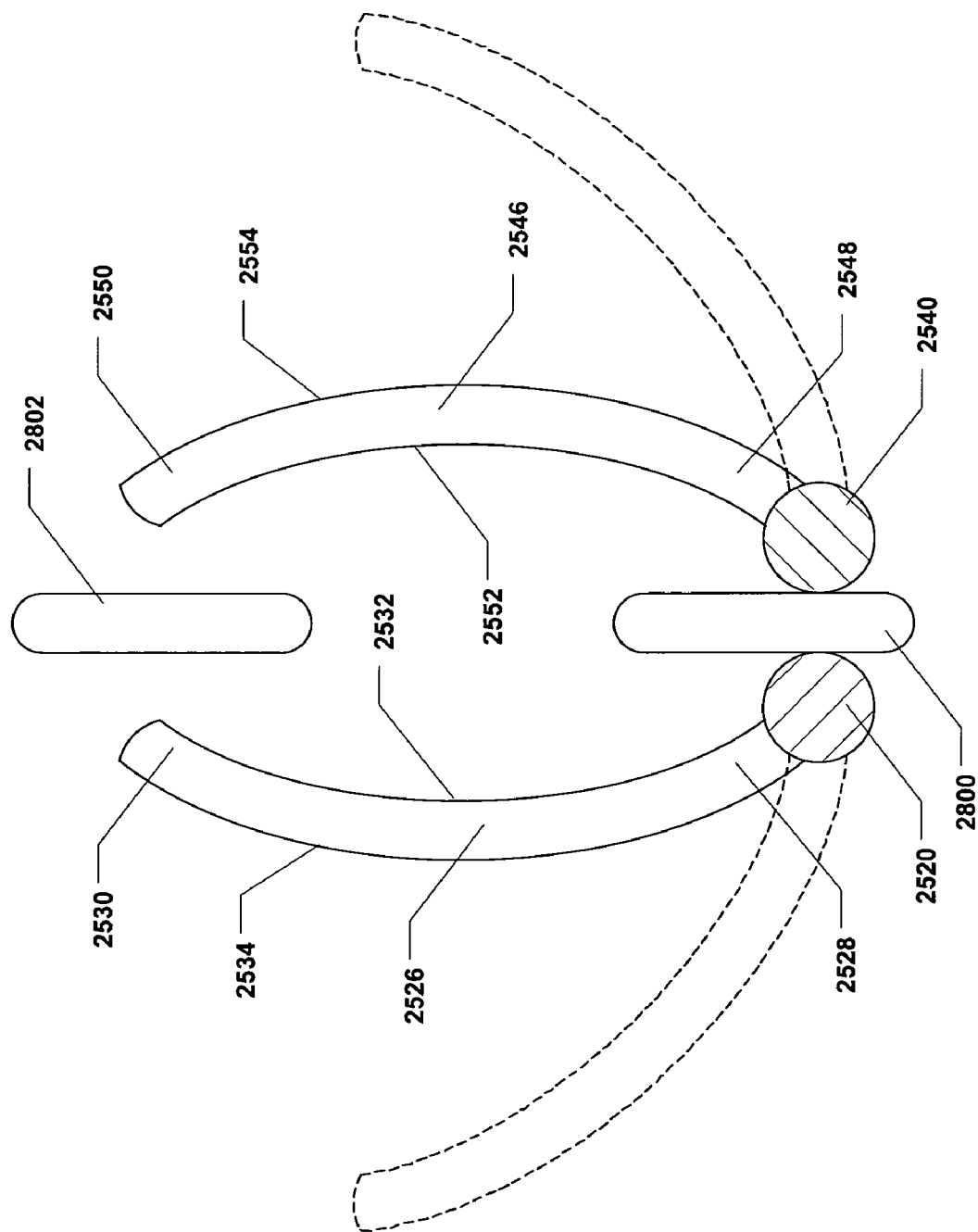
FIG. 28 is a cross-section view of the second molding device installed around adjacent spinous processes.

In a particular embodiment, as shown in FIG. 27 and FIG. 28, the molding device 2500 can be moved between an open position, indicated in dashed lines, and a closed position, indicated in solid lines. Further, as shown in FIG. 28, the molding device 2500 can be placed along a patient's spine and moved from the open position to the closed position. In the closed position, the proximal end 2528, 2548 of each mold component 2526, 2546 can be near a first spinous process 2800. Further, the distal end 2530, 2550 of each mold component 2526, 2546 can be near a second spinous process 2802.

As illustrated in FIG. 28, in the closed position, the interior surfaces 2532, 2552 of the mold components 2526, 2546 and the spinous processes 2800, 2802 can create a volume into which an expandable interspinous process implant can be molded, as described herein.

Description of a Second Method of Treating a Spine

Figure 29:
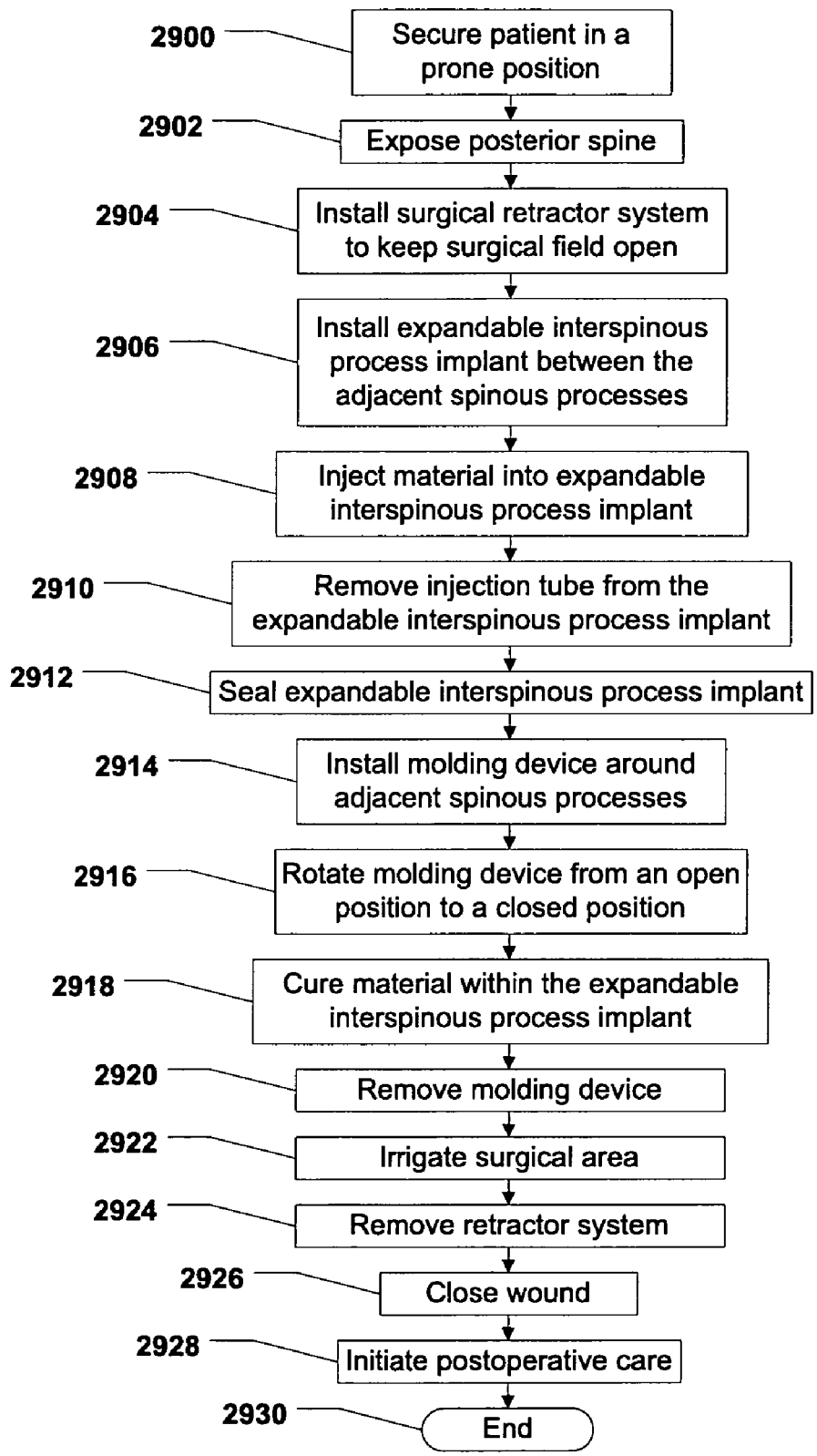
FIG. 29 is a flow chart illustrating a second method of treating a spine.

Referring to FIG. 29, a second method of treating a spine is shown and commences at block 2900. At block 2900, a patient can be secured in a prone position, e.g., on an operating table. At block 2902, the posterior spine can be exposed in order to expose adjacent spinous processes. Further, at block 2904, a surgical retractor system can be installed to keep a surgical field open.

Moving to block 2906, an expandable interspinous process implant can be installed between the adjacent spinous processes. In a particular embodiment, the expandable interspinous process implant can be an expandable interspinous process implant according to one or more of the embodiments described herein. At block 2908, an injectable biocompatible material can be injected into the expandable interspinous process implant. In a particular embodiment, the injectable biocompatible material can be one or more of the materials described herein.

Proceeding to block 2910, an injection tube can be removed from the expandable interspinous process implant. Thereafter, at bock 2912, the expandable interspinous process implant can be sealed. In a particular embodiment, the expandable interspinous process implant can be sealed by curing the material within the expandable interspinous process implant. Alternatively, a plug, a dowel, or another similar device can be used to seal the expandable interspinous process implant. Further, a one-way valve can be incorporated into the expandable interspinous process implant and can allow material to be injected into the expandable interspinous process implant, but prevent the same material from being expelled from the expandable interspinous process implant.

At block 2914, a molding device can be inserted around two adjacent spinous processes. In a particular embodiment, the molding device can be a molding device according to one or more of the embodiments described herein. Continuing to block 2916, the molding device is rotated from an open position to a closed position around the expandable interspinous process. Accordingly, the expandable interspinous process can be molded by the molding device and substantially conform a volume bound by the molding device and the spinous processes.

Proceeding to block 2918, the material within the expandable interspinous process implant can be cured. In a particular embodiment, the material within the expandable interspinous process implant can cure naturally, i.e., under ambient conditions, in situ. Alternatively, the material within the expandable interspinous process implant can be cured in situ using an energy source. For example, the energy source can be a light source that emits visible light, infrared (IR) light, or ultraviolet (UV) light. Further, the energy source can be a heating device, a radiation device, or other mechanical device.

At to block 2920, the molding device can be removed from around the spinous processes and the expandable interspinous process implant. Thereafter, at block 2922, the surgical area can be irrigated. At block 2924, the retractor system can be removed. Further, at block 2926, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 2928, postoperative care can be initiated. The method can end at state 2930.

In a particular embodiment, the spinous processes can be distracted prior to inserting the expandable interspinous process implant and the molding device. After the expandable interspinous process implant is inflated, molded, and cured as described herein, the distractor can be removed and the expandable interspinous process implant can support the superior spinous process and the inferior spinous process and substantially prevent a distance between the superior spinous process and the inferior spinous process from returning to a pre-distraction value.

Description of a Third Molding Device

Referring now to FIG. 30 through FIG. 35, a third embodiment of a molding device is shown and is generally designated 3000. As shown, the molding device 3000 includes a body 3002 that can include a proximal end 3004 and a distal end 3006. A handle 3008 can be attached to the proximal end 3004 of the body 3002.

Figure 30:
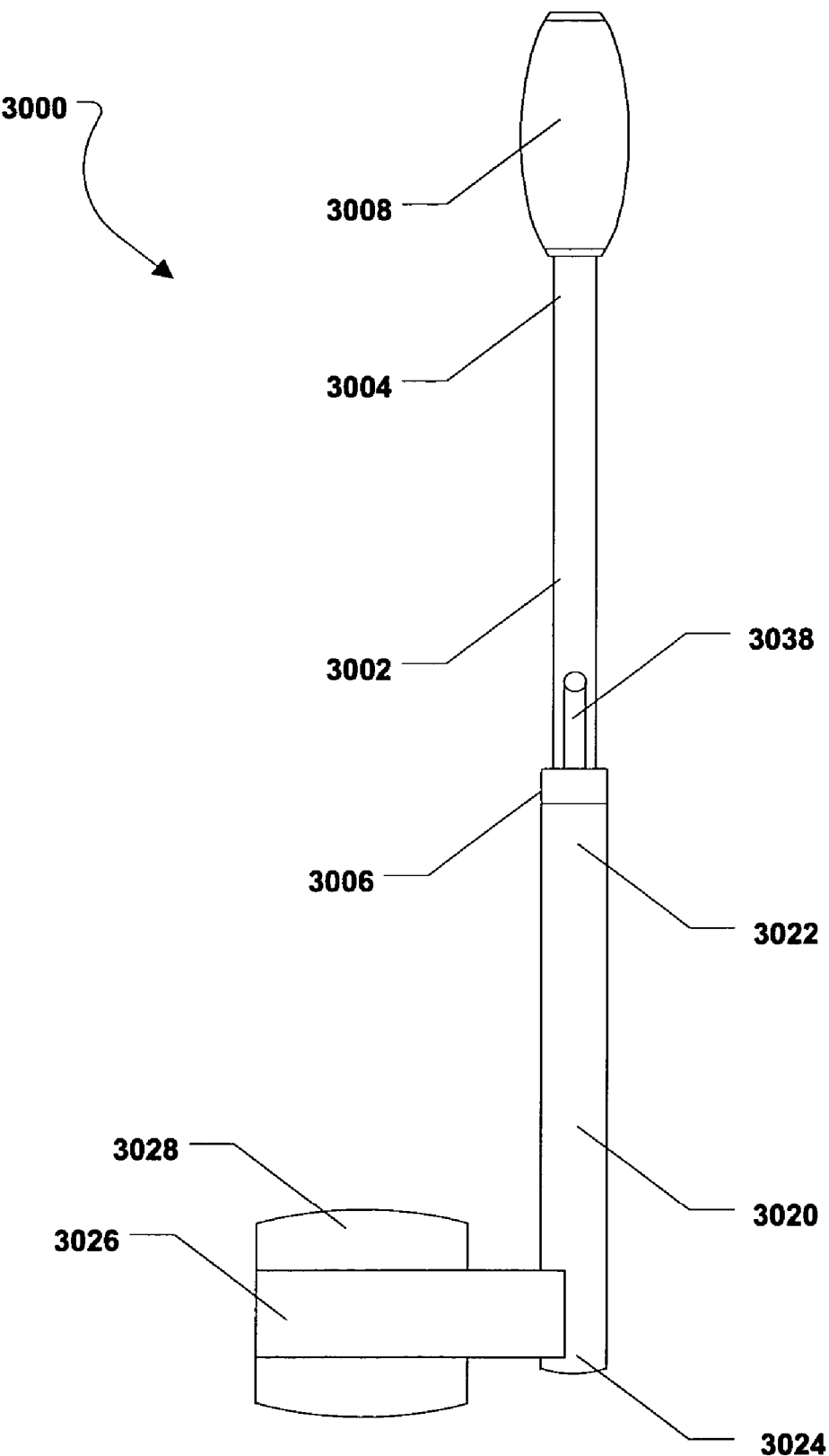
FIG. 30 is a side plan view of a third molding device.
Figure 31:
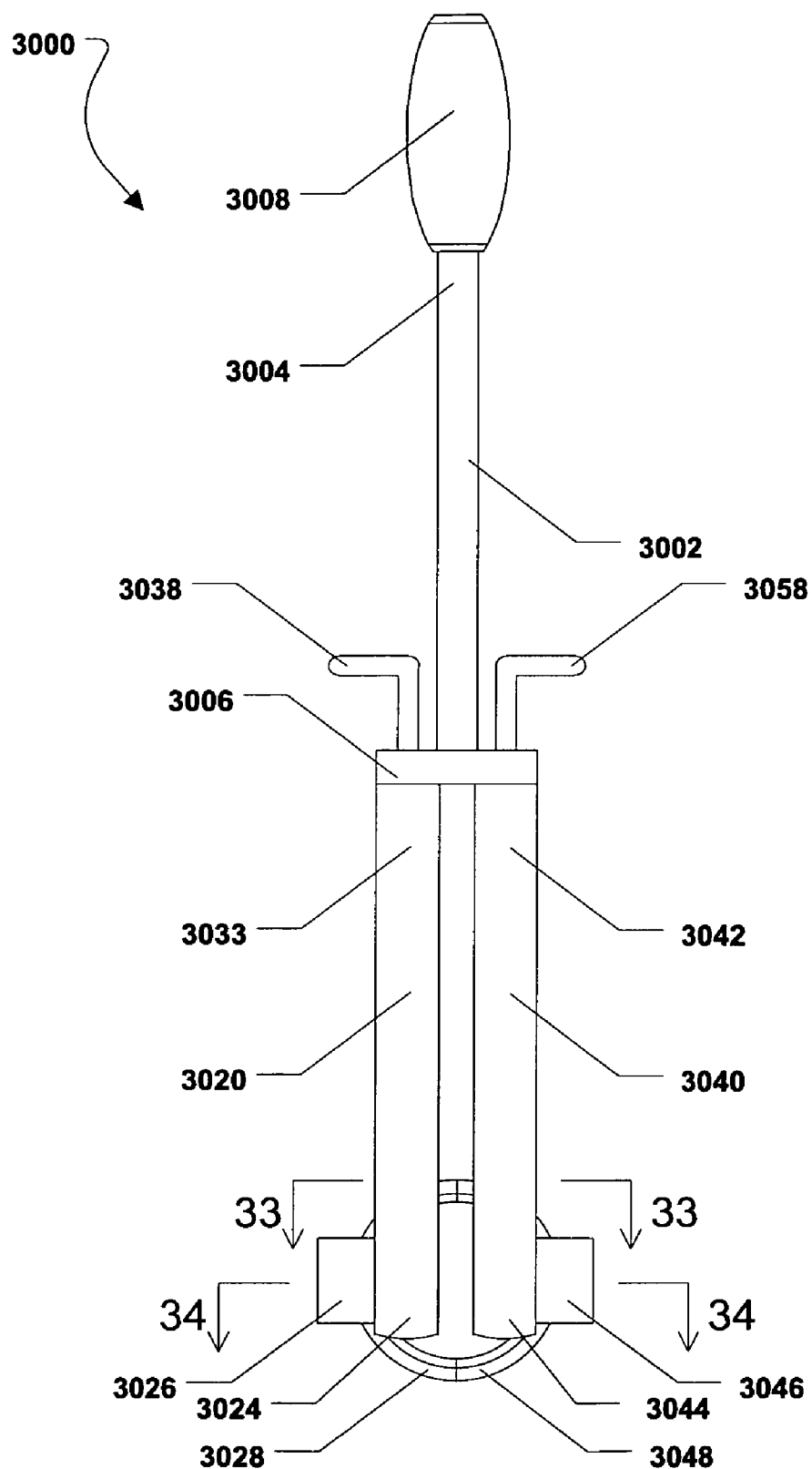
FIG. 31 is a rear plan view of the third molding device.
Figure 32:
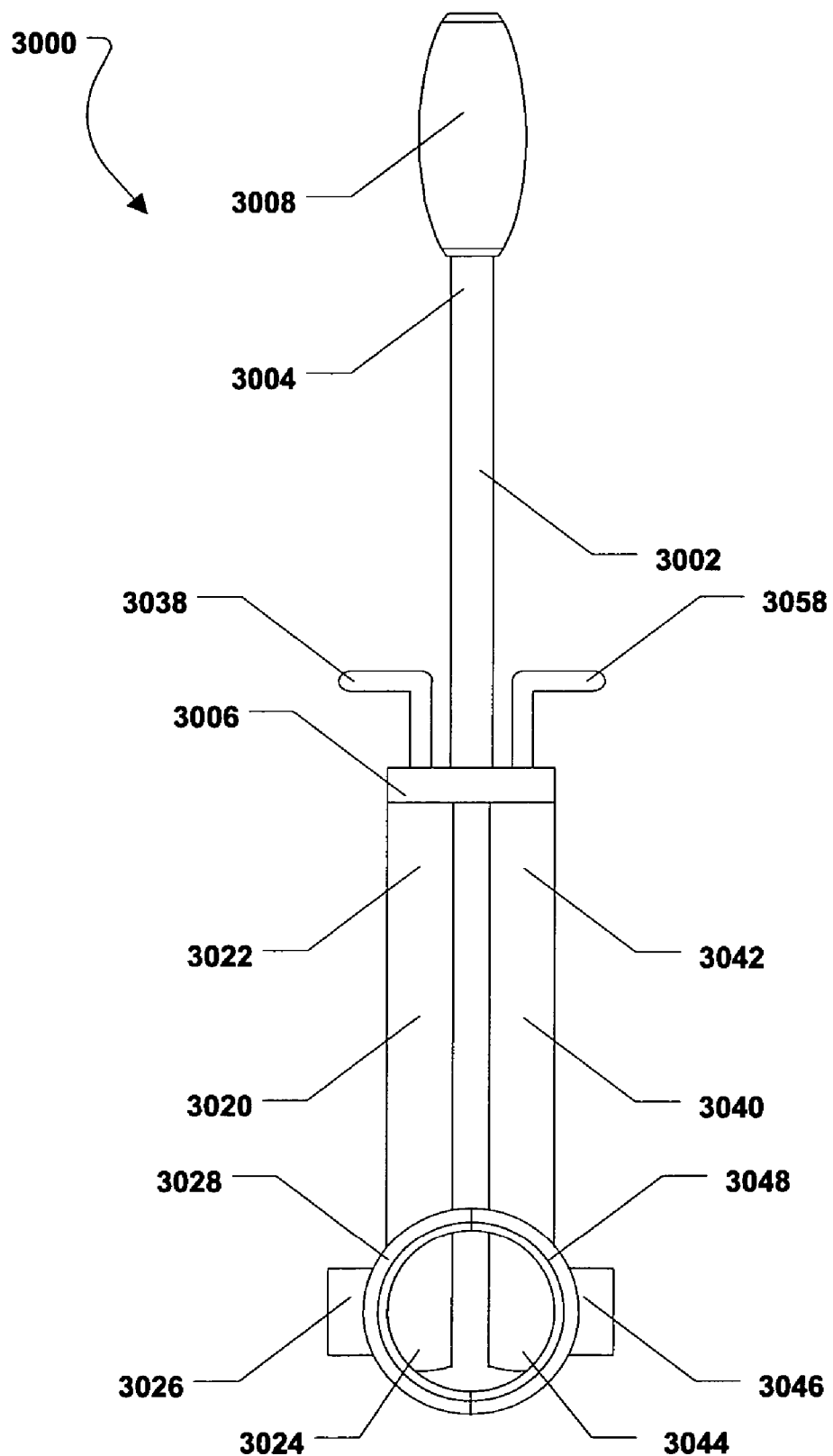
FIG. 32 is a front plan view of the third molding device.

FIG. 30 through FIG. 32 indicate that a first support post 3020 can extend from the distal end 3006 of the body 3002. Specifically, the first support post 3020 can include a proximal end 3022 and a distal end 3024 and the proximal end 3022 of the first support post 3020 can be rotably engaged with the distal end 3006 of the body 3002.

Figure 33:
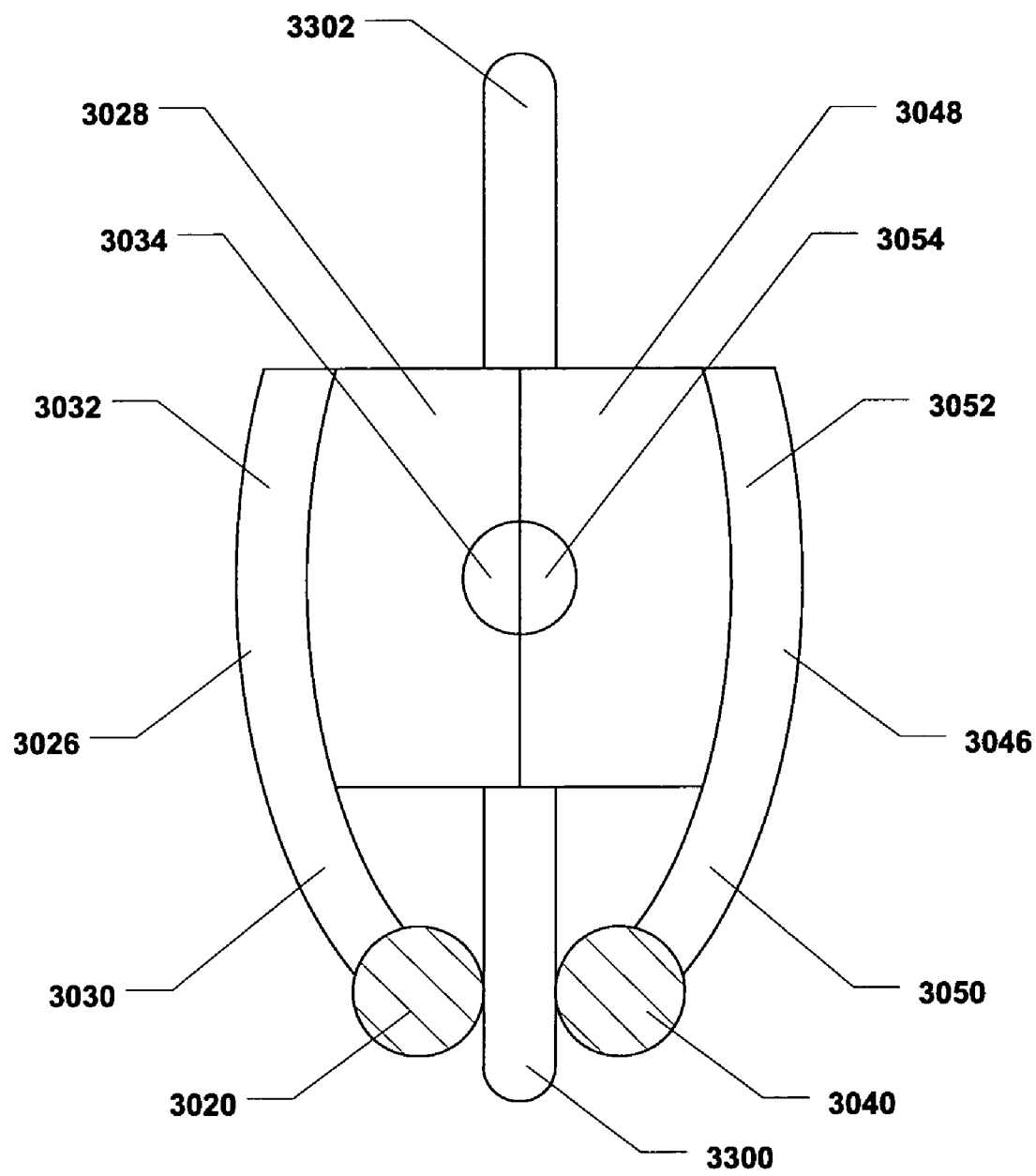
FIG. 33 is a cross-section view of the third molding device in a closed position taken along line 33-33 in FIG. 31.
Figure 34:
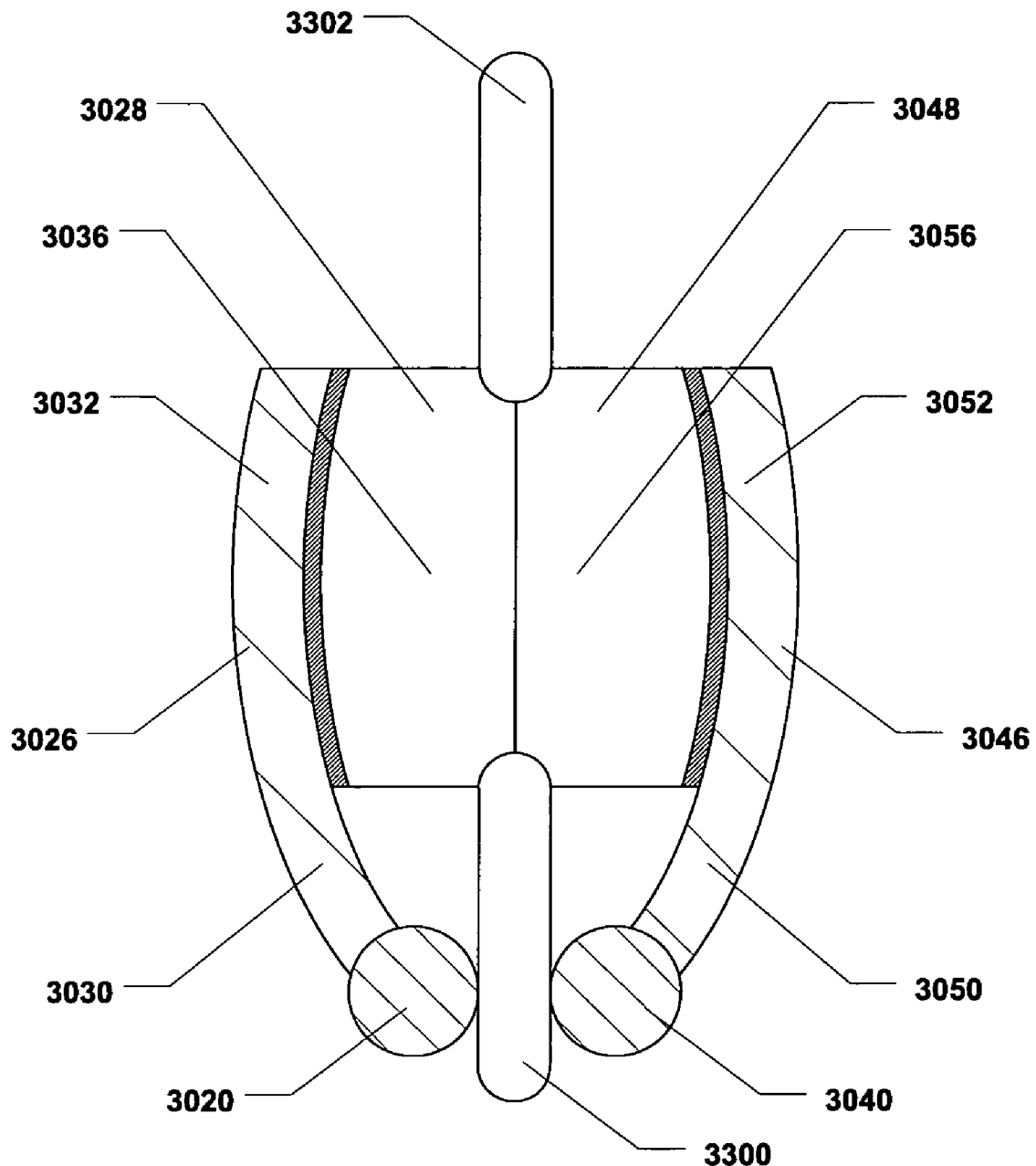
FIG. 34 is another cross-section view of the third molding device in a closed position taken along line 34-34 in FIG. 31.
Figure 35:
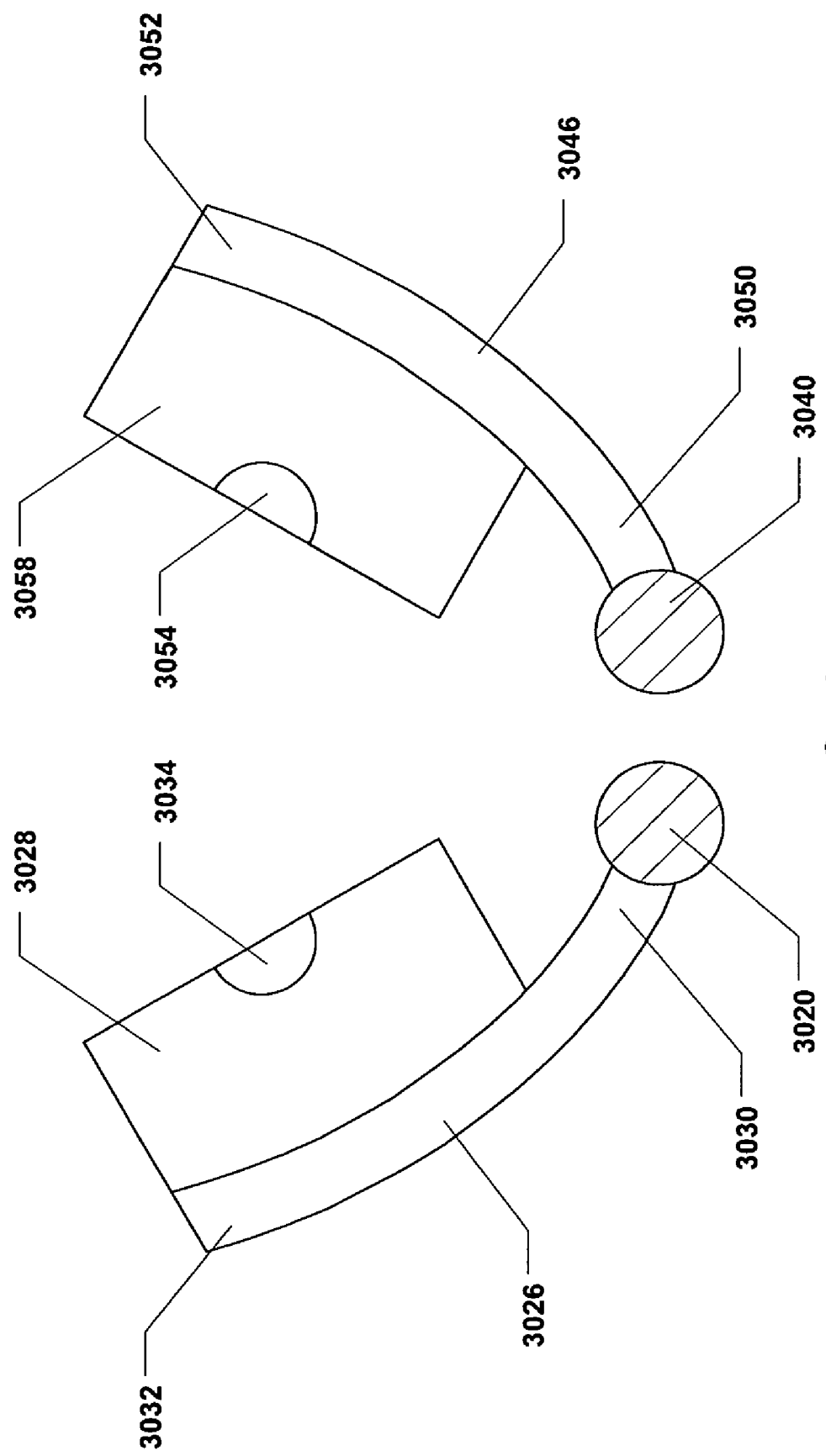
FIG. 35 is a cross-section view of the third molding device in an open position.

Moreover, a first arm 3026 can be attached to, or otherwise extend from, the distal end 3024 of the first support post 3020. Further, a first mold component 3028 can be attached to the first arm 3026. As shown in FIG. 33 through FIG. 35, the first arm 3026 can include a proximal end 3030 and a distal end 3032. FIG. 33 and FIG. 35 indicate that the first mold component 3028 can include an opening 3034. Moreover, as indicated in FIG. 34, the first mold component 3028 can include an interior surface 3036.

As shown in FIG. 19 and FIG. 30, a first handle 3038 can extend from the proximal end 3022 of the first support post 3020. The first handle 3038 can be used to rotate the first support post 3020 relative to the body 3002.

FIG. 30 and FIG. 32 indicate that a second support post 3040 can extend from the distal end 3006 of the body 3002.

Specifically, the second support post 3040 can include a proximal end 3042 and a distal end 3044 and the proximal end 3042 of the second support post 3040 can be rotably engaged with to the distal end 3006 of the body 3002.

Moreover, a second arm 3046 can be attached to, or otherwise extend from, the distal end 3044 of the second support post 3040. Further, a second mold component 3048 can be attached to the second arm 3046. As shown in FIG. 33 through FIG. 35, the second arm 3046 can include a proximal end 3050 and a distal end 3052. FIG. 33 and FIG. 35 indicate that the second mold component 3048 can include an opening 3054. Moreover, as indicated in FIG. 34, the second mold component 3048 can include an interior surface 3056.

As shown in FIG. 19 and FIG. 30, a second handle 3058 can extend from the proximal end 3042 of the first support post 3040. The second handle 3056 can be used to rotate the second support post 3040 relative to the body 3002.

In a particular embodiment, the molding device 3000 can be moved between a closed position, shown in FIG. 33 and FIG. 34, and an open position, shown in FIG. 35. Further, as shown in FIG. 33 and FIG. 34, the molding device 3000 can be placed along a patient's spine and moved from the open position to the closed position. In the closed position, the proximal end 3030, 3050 of each arm 3026, 3046 can be near a first spinous process 3300. Further, the distal end 3032, 3052 of each arm 3026, 3046 can be near a second spinous process 3302.

As illustrated in FIG. 34, in the closed position, the interior surfaces 3036, 3056 of the mold components 3028, 3048 and the spinous processes 3300, 3302 can create a volume into which an expandable interspinous process implant can be molded, as described herein. Additionally, in the closed position, the mold components 3028, 3048 create an open ended, barrel-shaped mold that can constrain expansion of an expandable process implant in a radial direction, relative to the mold. However, the mold components 3028, 3048 can allow expansion of the expandable process implant in a longitudinal direction, relative to the mold. Accordingly, as the expandable process implant is inflated, it can expand through the open ends of the mold components 3028, 3048 and distract the spinous processes 3300, 3302.

Also, in a particular embodiment, the openings 3034, 3054 formed in the mold components 3028, 3048 can allow the mold components 3028, 3048 to be closed around an injection tube of the expandable interspinous process implant.

Description of a Third Method of Treating a Spine

Figure 36:
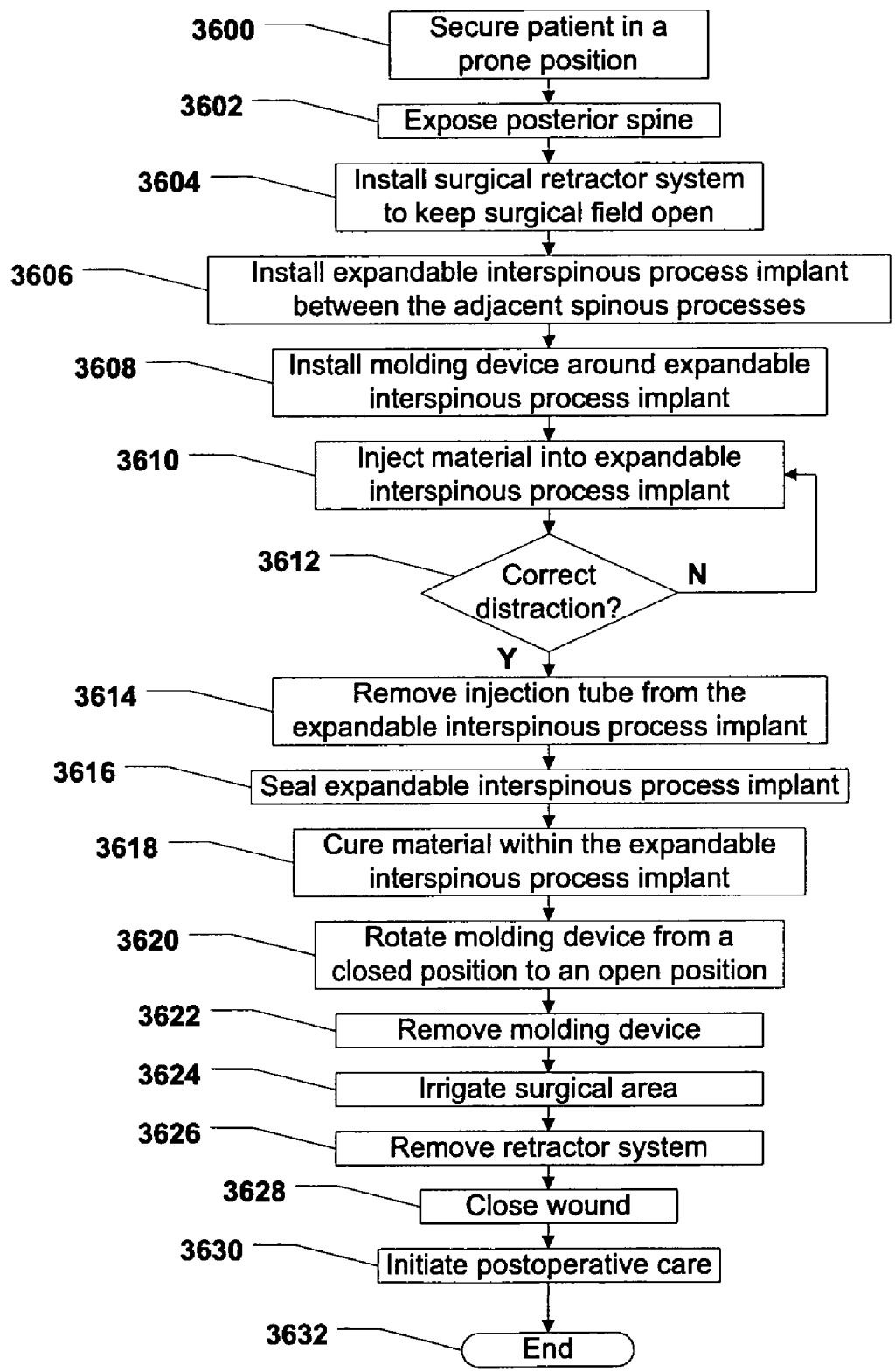
FIG. 36 is a flow chart illustrating a third method of treating a spine.

Referring to FIG. 36, a third method of treating a spine is shown and commences at block 3600. At block 3600, a patient can be secured in a prone position, e.g., on an operating table. At block 3602, the posterior spine can be exposed in order to expose adjacent spinous processes. Further, at block 3604, a surgical retractor system can be installed to keep a surgical field open.

Moving to block 3606, an expandable interspinous process implant can be installed between the adjacent spinous processes. In a particular embodiment, the expandable interspinous process implant can be an expandable interspinous process implant according to one or more of the embodiments described herein. At block 3608, a molding device can be installed around the expandable interspinous process implant. In a particular embodiment, the molding device can be a molding device according to one or more of the embodiments described herein.

At block 3610, an injectable biocompatible material can be injected into the expandable interspinous process implant. In a particular embodiment, the injectable biocompatible material can be one or more of the materials described herein.

Continuing to decision step 3612, it can be determined whether a distraction of a superior spinous process and an inferior spinous process is correct. If not, the method can return to block 3610 and additional material can be injected into the expandable interspinous process implant. Thereafter, the method can proceed as described herein. If the distraction is correct, the method can proceed to block 3614.

At block 3614, an injection tube can be removed from the expandable interspinous process implant. Thereafter, at bock 3616, the expandable interspinous process implant can be sealed. In a particular embodiment, the expandable interspinous process implant can be sealed by curing the material within the expandable interspinous process implant. Alternatively, a plug, a dowel, or another similar device can be used to seal the expandable interspinous process implant. Further, a one-way valve can be incorporated into the expandable interspinous process implant and can allow material to be injected into the expandable interspinous process implant, but prevent the same material from being expelled from the expandable interspinous process implant.

Proceeding to 3618, the material within the expandable interspinous process implant can be cured. In a particular embodiment, the material within the expandable interspinous process implant can cure naturally, i.e., under ambient conditions, in situ. Alternatively, the material within the expandable interspinous process implant can be cured in situ using an energy source. For example, the energy source can be a light source that emits visible light, infrared (IR) light, or ultraviolet (UV) light. Further, the energy source can be a heating device, a radiation device, or other mechanical device.

At to block 3620, the molding device can be rotated from a closed position to an open position. Next, at block 3622, the molding device can be removed from around the spinous processes and the expandable interspinous process implant. Moving to block 3624, the surgical area can be irrigated. At block 3626, the retractor system can be removed. Further, at block 3628, the surgical wound can be closed. The surgical wound can be closed by simply allowing the patient's skin to close due to the elasticity of the skin. Alternatively, the surgical wound can be closed using sutures, surgical staples, or any other suitable surgical technique well known in the art. At block 3630, postoperative care can be initiated. The method can end at state 3632.

In a particular embodiment, the spinous processes can be distracted prior to inserting the expandable interspinous process implant and the molding device. After the expandable interspinous process implant is inflated, molded, and cured as described herein, the distractor can be removed and the expandable interspinous process implant can support the superior spinous process and the inferior spinous process and substantially prevent a distance between the superior spinous process and the inferior spinous process from returning to a pre-distraction value.

CONCLUSION

With the configuration of structure described above, the molding device for an expandable interspinous process implant provides a device that can be used to mold an implant along a patient's spine and substantially alleviate or minimize one or more symptoms associated with disc degeneration, facet joint degeneration, or a combination thereof. For example, an expandable interspinous process implant can be installed between adjacent spinous processes, expanded, molded, and cured in order to support the spinous processes and maintain them at or near a predetermined distance there between.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method of treating a spine, comprising:
installing an expandable interspinous process implant between a superior spinous process and an inferior spinous process;
installing distinct first and second portions of a molding device around the expandable interspinous process implant such that:
the first portion laterally limits the implant and is disposed on a first lateral side of the sagittal plane defined by the superior and inferior spinous processes;
the second portion laterally limits the implant and is disposed on a second opposite lateral side of the sagittal plane;
expanding the expandable interspinous process implant;
removing the first and second portions of the molding device from around the interspinous process implant while maintaining the expanded interspinous process implant between the superior and inferior spinous processes;
wherein the expandable interspinous process implant at least partially conforms to a volume bound by the molding device, the superior spinous process, and the inferior spinous process; and
further comprising curing an injectable biocompatible material within the expandable interspinous process implant.

2. A method of treating a spine, comprising:
installing an expandable interspinous process implant between a superior spinous process and an inferior spinous process;
installing distinct first and second portions of a molding device around the expandable interspinous process implant such that:
the first portion laterally limits the implant and is disposed on a first lateral side of the sagittal plane defined by the superior and inferior spinous processes;
the second portion laterally limits the implant and is disposed on a second opposite lateral side of the sagittal plane;
expanding the expandable interspinous process implant;
removing the first and second portions of the molding device from around the interspinous process implant while maintaining the expanded interspinous process implant between the superior and inferior spinous processes:
wherein said installing comprises rotating the molding device from a closed position to an open position.

3. A method of treating a spine, comprising:
installing an expandable interspinous process implant between a superior spinous process and an inferior spinous process;
installing distinct first and second portions of a molding device around the expandable interspinous process implant such that:
the first portion laterally limits the implant and is disposed on a first lateral side of the sagittal plane defined by the superior and inferior spinous processes;
the second portion laterally limits the implant and is disposed on a second opposite lateral side of the sagittal plane;
expanding the expandable interspinous process implant;
removing the first and second portions of the molding device from around the interspinous process implant while maintaining the expanded interspinous process implant between the superior and inferior spinous processes;
wherein expanding the implant occurs prior to said installing the first and second portions of the molding device.

4. A method of treating a spine, comprising:
installing an expandable interspinous process implant between a superior spinous process and an inferior spinous process;
installing distinct first and second portions of a molding device around the expandable interspinous process implant such that:
the first portion laterally limits the implant and is disposed on a first lateral side of the sagittal plane defined by the superior and inferior spinous processes;
the second portion laterally limits the implant and is disposed on a second opposite lateral side of the sagittal plane;
expanding the expandable interspinous process implant;
removing the first and second portions of the molding device from around the interspinous process implant while maintaining the expanded interspinous process implant between the superior and inferior spinous processes;
further comprising adding a curable fluid through an injection tube into the implant;
removing the injection tube from the implant, wherein removing the injection tube occurs prior to installing the molding device.

5. A method of treating a spine, comprising:
installing an expandable interspinous process implant between a superior spinous process and an inferior spinous process;
installing distinct first and second portions of a molding device around the expandable interspinous process implant such that:
the first portion laterally limits the implant and is disposed on a first lateral side of the sagittal plane defined by the superior and inferior spinous processes;
the second portion laterally limits the implant and is disposed on a second opposite lateral side of the sagittal plane;
expanding the expandable interspinous process implant;
removing the first and second portions of the molding device from around the interspinous process implant while maintaining the expanded interspinous process implant between the superior and inferior spinous processes;
wherein said expanding the implant distracts the superior and inferior spinous processes.

* * * * *